(12) United States Patent
Volpe

(10) Patent No.: US 12,089,967 B2
(45) Date of Patent: Sep. 17, 2024

(54) EXTERNAL MEDICAL DEVICE THAT IDENTIFIES A RESPONSE ACTIVITY

(71) Applicant: ZOLL Medical Corporation, Chelmsford, MA (US)

(72) Inventor: Shane Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 481 days.

(21) Appl. No.: 17/336,433

(22) Filed: Jun. 2, 2021

(65) Prior Publication Data

US 2021/0282722 A1    Sep. 16, 2021

Related U.S. Application Data

(63) Continuation of application No. 15/393,616, filed on Dec. 29, 2016, now Pat. No. 11,064,952.
(Continued)

(51) Int. Cl.
*A61B 5/00* (2006.01)
*A61B 5/11* (2006.01)
(Continued)

(52) U.S. Cl.
CPC .......... *A61B 5/7282* (2013.01); *A61B 5/1124* (2013.01); *A61B 5/162* (2013.01);
(Continued)

(58) Field of Classification Search
CPC .......... A61N 1/39–3993; A61N 1/3625; A61N 1/0456; A61N 1/36014; A61N 1/3603; A61N 1/36031; A61N 1/36034; A61N 1/36514; A61N 1/36535; A61N 1/36542; A61N 1/36585; A61N 1/0484; A61N 1/046; A61B 5/0006; A61B 5/4836; A61B 5/6823; A61B 5/332; A61B 5/363;
(Continued)

(56) References Cited

U.S. PATENT DOCUMENTS 3,942,534 A    3/1976 Allen et al.
4,928,690 A    5/1990 Heilman et al.
(Continued)

OTHER PUBLICATIONS

Leong et al., "Prognostic value of grip strength: findings from the Prospective Urban Rural Epidemiology (PURE) study", Lancet, Jul. 18, 2015, pp. 266-273, vol. 386.
(Continued)

*Primary Examiner* — David J. McCrosky
(74) *Attorney, Agent, or Firm* — The Webb Law Firm

(57) ABSTRACT

An external medical device is provided. The device can include monitoring circuitry configured to sense physiological information of a patient and a controller with one or more input components. The controller can be configured to: detect one or more patient events based, at least in part, on the physiological information; notify the patient of the detection of the one or more patient events; and receive a patient response to the notification. The patient response can include a response activity identifiable by the input component, which is configured to test a psychomotor ability of the patient, cognitive ability of the patient, strength, balance, stability, and flexibility of the patient, and/or to substantially confirm that a person performing the activity is the patient.

20 Claims, 14 Drawing Sheets

Related U.S. Application Data

(60) Provisional application No. 62/272,818, filed on Dec. 30, 2015.

(51) Int. Cl.

| | | |
|---|---|---|
| *A61B 5/16* | (2006.01) | |
| *A61B 5/349* | (2021.01) | |
| *A61N 1/04* | (2006.01) | |
| *A61N 1/39* | (2006.01) | |
| *G06F 3/04817* | (2022.01) | |
| *G06F 3/04883* | (2022.01) | |
| *G10L 15/22* | (2006.01) | |
| *G10L 25/66* | (2013.01) | |

(52) U.S. Cl.
CPC ............ *A61B 5/349* (2021.01); *A61B 5/6804* (2013.01); *A61B 5/6823* (2013.01); *A61B 5/74* (2013.01); *A61B 5/7475* (2013.01); *A61N 1/3904* (2017.08); *A61N 1/3925* (2013.01); *G06F 3/04817* (2013.01); *G06F 3/04883* (2013.01); *A61N 1/046* (2013.01); *A61N 1/0484* (2013.01); *A61N 1/3993* (2013.01); *G10L 15/22* (2013.01); *G10L 25/66* (2013.01)

(58) Field of Classification Search
CPC ......... A61B 5/361; A61B 5/366; A61B 5/349; A61B 5/316; A61B 5/6805; A61B 5/721; A61B 5/7282; A61B 5/1123; A61B 5/117
See application file for complete search history.

(56) References Cited

U.S. PATENT DOCUMENTS

| | | |
|---|---|---|
| 5,078,134 A | 1/1992 | Heilman et al. |
| 5,741,306 A | 4/1998 | Glegyak et al. |
| 5,944,669 A | 8/1999 | Kaib |
| 6,065,154 A | 5/2000 | Hulings et al. |
| 6,154,673 A | 11/2000 | Morgan et al. |
| 6,253,099 B1 | 6/2001 | Oskin et al. |
| 6,280,461 B1 | 8/2001 | Glegyak et al. |
| 6,681,003 B2 | 1/2004 | Inder et al. |
| 7,996,887 B2 | 8/2011 | Garbow et al. |
| 8,271,082 B2 | 9/2012 | Donnelly et al. |
| 8,369,944 B2 | 2/2013 | Macho et al. |
| 8,676,313 B2 | 3/2014 | Volpe et al. |
| 9,352,166 B2 | 5/2016 | Sullivan et al. |
| 9,757,579 B2 * | 9/2017 | Foshee, Jr. .............. A61B 5/363 |
| 9,827,435 B2 | 11/2017 | Walker et al. |
| 10,750,996 B2 * | 8/2020 | Wariar .................. A61B 5/686 |
| 2013/0325078 A1 * | 12/2013 | Whiting ................ A61B 5/361 |
| | | 607/7 |
| 2013/0325096 A1 | 12/2013 | Dupelle et al. |
| 2014/0025129 A1 | 1/2014 | Abbenhouse et al. |
| 2014/0025131 A1 | 1/2014 | Sullivan et al. |
| 2014/0043149 A1 | 2/2014 | Cowan et al. |
| 2014/0094865 A1 | 4/2014 | Walker et al. |
| 2014/0094866 A1 | 4/2014 | Walker et al. |
| 2015/0039053 A1 * | 2/2015 | Kaib .................... A61N 1/3993 |
| | | 607/63 |
| 2015/0290469 A1 | 10/2015 | Sullivan et al. |
| 2016/0004831 A1 | 1/2016 | Carlson et al. |
| 2017/0021184 A1 | 1/2017 | Pavel et al. |
| 2017/0154178 A1 | 6/2017 | Hamasaki |
| 2017/0296107 A1 | 10/2017 | Reid et al. |

OTHER PUBLICATIONS

Park et al., "A study on password input method using authentication pattern and puzzle", 2011 6th International Conference Computer Sciences and Convergence Information Technology (ICCIT), IEEE, 2011.

* cited by examiner

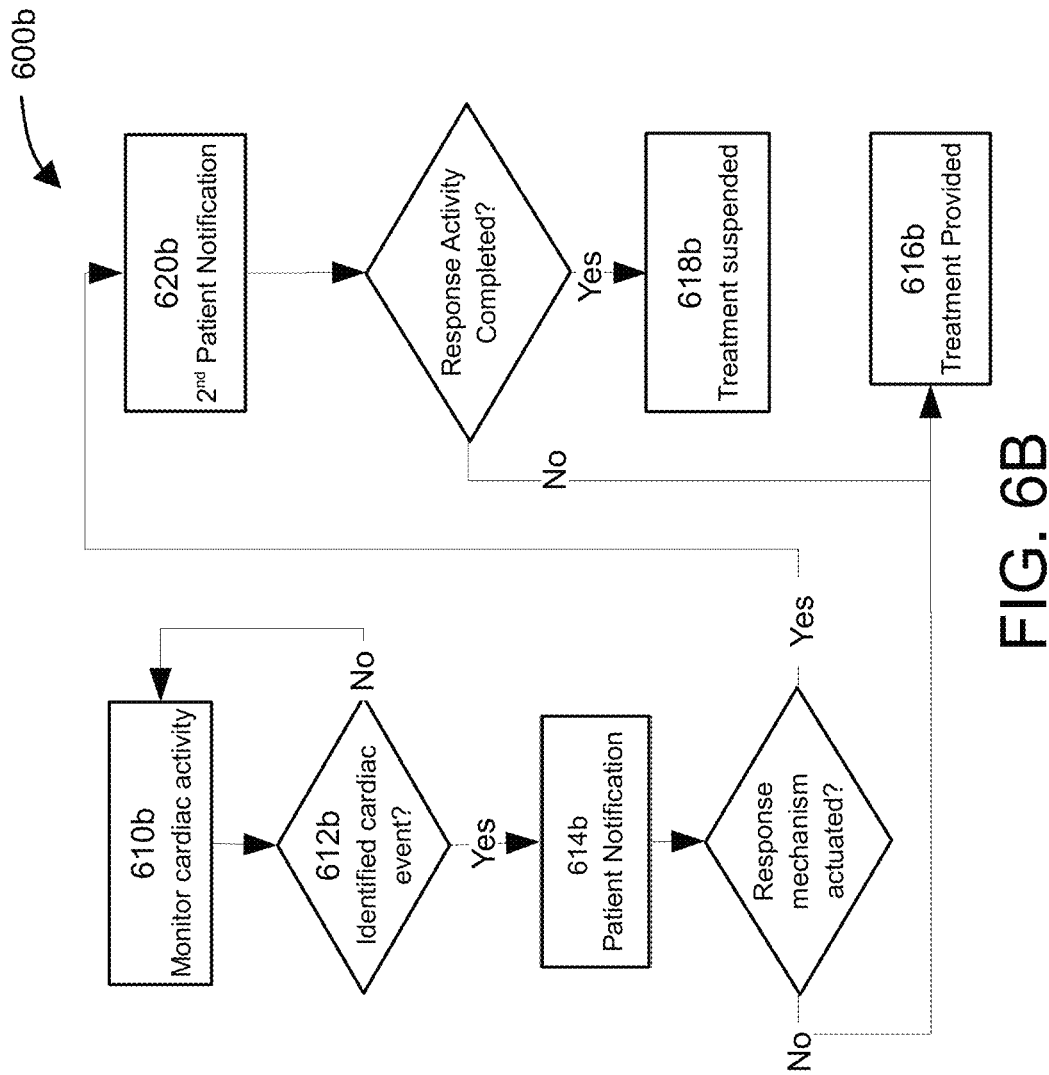

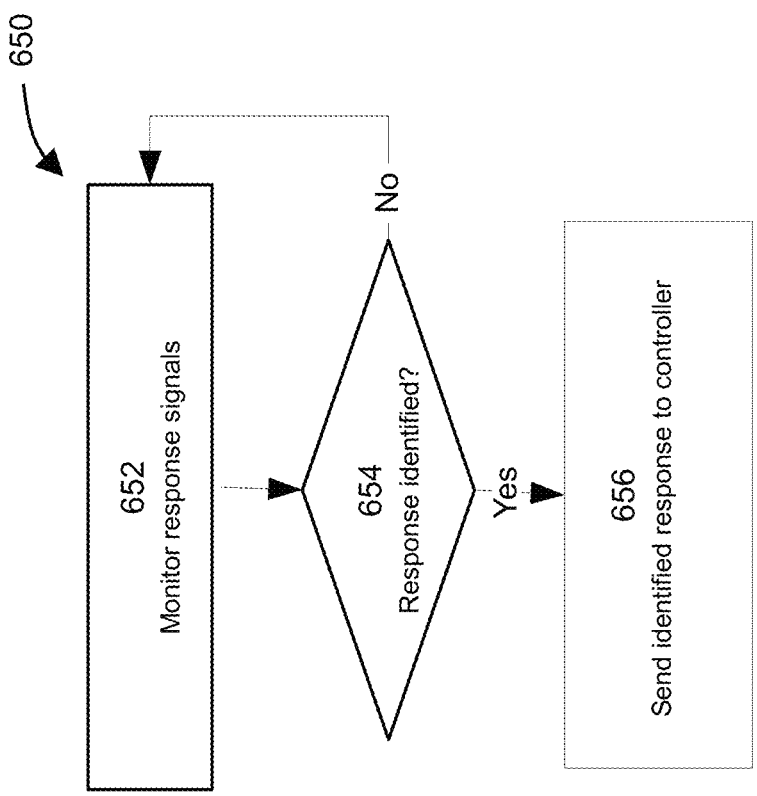

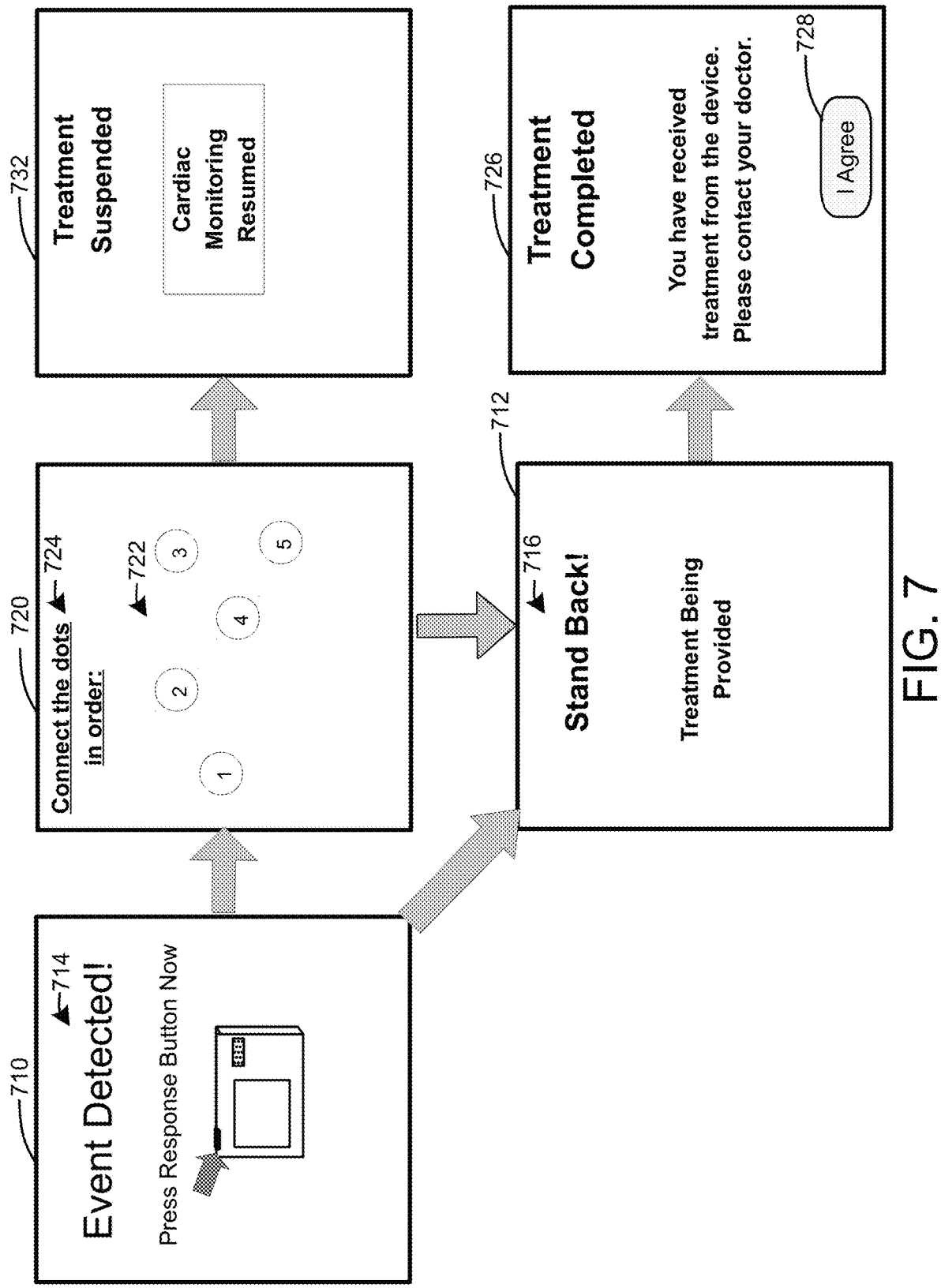

EXTERNAL MEDICAL DEVICE THAT IDENTIFIES A RESPONSE ACTIVITY

CROSS REFERENCE TO RELATED APPLICATIONS

This application is a continuation of U.S. patent application Ser. No. 15/393,616, entitled "External Medical Device that Identifies a Response Activity", filed on Dec. 29, 2016, which claims priority to U.S. Provisional Patent Application No. 62/272,818 filed Dec. 30, 2015, entitled "External Medical Device that Identifies a Response Activity", the disclosure of each of which is hereby incorporated in its entirety by reference.

BACKGROUND

Technical Field

The present disclosure relates to an external medical device and, in some aspects, to an external medical device configured to identify a patient response activity and, in response to the identified activity, suspend or modify a treatment to be provided to the patient by the device.

Description of Related Art

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator. Monitoring devices are also available. For example, such devices operate by monitoring the patient's heart for treatable arrhythmias and, when a treatable arrhythmia is detected, the device applies corrective electrical pulses directly to the heart. Wearable pacing devices and/or defibrillators have been developed for a certain population of patients, e.g., those that may have recently experienced a heart attack, that are susceptible to heart arrhythmias and are at temporary risk of sudden death, or that are awaiting an implantable device. Monitoring devices can issue an alarm or alert Pacemakers, defibrillators, and other monitoring devices can be configured to attempt to identify, receive, or detect a patient response prior to providing treatment to the patient. Monitoring devices can also attempt to identify a patient response prior to issuing an alert or alarm indicative of a patient condition or event of interest. For example, a patient response can include pressing a button on the device to suspend treatment or to delay issuance of an alarm or alert.

SUMMARY

Preferred and non-limiting aspects or embodiments of the present invention will now be described in the following numbered clauses:

Clause 1. An external medical device comprises: monitoring circuitry configured to sense physiological information of a patient; and a controller comprising one or more input components. The controller can be configured to: detect one or more patient events based, at least in part, on the physiological information; notify the patient of the detection of the one or more patient events; and receive a patient response to the notification, the patient response comprising a response activity identifiable by the input component, the response activity configured to test a psychomotor ability of the patient.

Clause 2. The device of clause 1, wherein the one or more input components comprise at least one of: a response button; a touch screen; an audio detection device; a motion sensor; a contact sensor; a pressure sensor; a gesture recognition component; and a patient physiological sensor.

Clause 3. The device of clause 2, wherein the response activity identifiable by the touch screen comprises one or more of (a) drawing a shape on the touch screen; (b) drawing an alpha-numeric character on the touch screen; (c) dragging or moving an image on the touch screen display to another location on the touch screen; (d) tracing a shape or path on the touch screen; and (e) rotating or manipulating multiple icons or shapes on the touch screen display in a coordinated manner.

Clause 4. The device of clause 2 or clause 3, wherein the response activity identifiable by the gesture recognition component comprises one or more of: (a) performing a predetermined movement in response to an instruction received from the device; (b) maintaining a predetermined body or hand position for a predetermined period of time; (c) touching or tapping a portion of patient's body or the device in accordance with a predetermined pattern; and (d) performing a predetermined facial expression.

Clause 5. The device of any of clauses 2-4, wherein the response activity identifiable by the motion sensor comprises one or more of (a) performing a coordinated body movement in response to an instruction from the device, and (b) moving the device in a coordinated manner in response to an instruction from the device.

Clause 6. The device of any of clauses 2-5, wherein the response activity identifiable by the audio detection device comprises instructing the patient to speak and obtaining a voice recording of the patient's speech for analysis.

Clause 7. The device of clause 6, wherein instructing the patient to speak comprises instructing the patient to speak a predetermined phrase and analyzing the patient's voice recording with respect to a previously obtained version of the phrase spoken by the patient.

Clause 8. The device of any of clauses 1-7, wherein the controller is configured to identify one of a partial response activity and an incorrect response activity.

Clause 9. The device of clause 8, wherein the controller is configured to provide a follow-up notification when one of the partial response activity and the incorrect response activity are identified, the follow-up notification comprising one or more of: (a) an instruction to perform an activity requiring a different patient ability than the response activity that received one of the partial response and the incorrect response; (b) an instruction to perform a different activity requiring the same patient ability as the response activity that received one of the partial response and the incorrect response; (c) an instruction to perform a different activity having a same level of difficulty as the response activity that received one of the partial response and the incorrect response; and (d) an instruction to perform an activity having a lower level of difficulty than the response activity that received one of the partial response and the incorrect response.

Clause 10. The device of any of clauses 1-9, further comprising one or more treatment elements, and wherein the controller is configured to, based on the received response activity, suspend a therapy that is provided via the one or more treatment elements, to address the patient event.

Clause 11. The device of any of clauses 1-10 comprising at least one of a cardiac monitor, a defibrillator, and a wearable defibrillator.

Clause 12. The device of any of clauses 1-11, wherein the patient response further comprises a second response activity configured to confirm that a person performing the activity is the patient.

Clause 13. The device of clause 12, wherein the second response activity configured to confirm that a person performing the activity is the patient comprises one or more of: providing a predetermined passcode or keyphrase; providing a response to a security question preselected by the patient; and answering a question requiring patient-specific information.

Clause 14. An external medical device comprises: monitoring circuitry configured to sense physiological information of a patient; and a controller comprising one or more input components. The controller can be configured to: detect one or more patient events based, at least in part, on the physiological information; notify the patient of the detection of the patient event; and receive a patient response to the notification, the patient response comprising a response activity configured to substantially confirm that a person performing the activity is the patient.

Clause 15. The device of clause 14, wherein the response activity configured to substantially confirm that a person performing the activity is the patient comprises one or more of: (a) providing patient-identifying information that is not generally known; and (b) performing an identification activity.

Clause 16. The device of clause 15, wherein providing information that is not generally known comprises one or more of: providing a predetermined passcode or keyphrase; providing a response to a security question preselected by the patient; and providing a response to a question requiring patient-specific knowledge.

Clause 17. The device of clause 15 or clause 16, wherein performing a patient specific activity comprises: performing a touch screen activity representative of patient identity; touching or operating the device in a manner representative of patient identity; speaking a predetermined phrase that can be used by the device to confirm patient identity; and allowing the device to obtain an image of the patient that can be used by the device to confirm patient identity.

Clause 18. The device of any of clauses 14-17, further comprising one or more treatment elements, and wherein the controller is configured to, based on the received response activity, suspend a therapy that is provided via the one or more treatment elements, to address the patient event.

Clause 19. An external medical device comprises: monitoring circuitry configured to sense physiological information of a patient; and a controller comprising one or more input components. The controller can be configured to: detect one or more patient events based, at least in part, on the physiological information; notify the patient of the detection of the patient event; and receive a patient response to the notification, the patient response comprising a response activity configured to test cognitive ability of the patient.

Clause 20. The device of clause 19, wherein the response activity configured to test cognitive ability of the patient is based on one or more of general knowledge of the patient, short-term memory recall ability of the patient, problem solving and logical reasoning ability of the patient, and visual acumen of the patient.

Clause 21. The device of clause 20, wherein the response activity based on general knowledge of the patient comprises providing a response based on knowledge of one or more of: time/day/date information; current events information; visual recognition of shapes, colors, or pictures; recognition of sounds; and recognition of a haptic feedback pattern.

Clause 22. The device of clause 20 or clause 21, wherein the response activity based on memory recall comprises providing a response to a short-term memory test.

Clause 23. The device of any of clauses 20-22, wherein the response activity based on problem solving and logical reasoning ability of the patient comprises one or more of: providing a response requiring performance of arithmetic; providing a response based on reading comprehension; and providing a response to one of a logic game, riddle, and puzzle.

Clause 24. The device of any of clauses 19-23, wherein the patient response further comprises a second response activity configured to test one or more of strength, balance, stability, and flexibility of the patient.

Clause 25. An external medical device comprises: monitoring circuitry configured to sense physiological information of a patient; and a controller comprising one or more input components. The controller can be configured to: detect one or more patient events based, at least in part, on the physiological information; notify the patient of the detection of the patient event; and receive a patient response to the notification, the patient response comprising a response activity configured to test one or more of strength, balance, stability, and flexibility of the patient.

Clause 26. The device of clause 25, wherein the input components comprise one or more of: a response button; a touch screen; an audio detection device; a motion sensor; an optical sensor; a contact sensor; a pressure sensor; a gesture recognition component; and a patient physiological sensor.

Clause 27. The device of clause 26, wherein the response activity that is identifiable by one or more of a motion sensor, an optical sensor, and a physiological sensor comprises one or more of: standing up; walking; picking up and/or moving the device; tapping a portion of the device; tapping a portion of the patient's body; maintaining a portion of the patient's body in stable position for a predetermined period of time; clapping hands; and stomping feet.

Clause 28. The device of clause 26 or clause 27, wherein the response activity identifiable by a pressure sensor and/or a contact sensor comprises one or more of: pressing against a portion of the device for a predetermined duration; pressing against a portion of the device with a force above a predetermined threshold; pressing against another object for a predetermined duration; and pressing against another object with a force above a predetermined threshold.

Clause 29. An external medical device comprising: monitoring circuitry configured to sense physiological information of a patient; and a controller comprising one or more input components. The controller configured to: detect one or more patient events based, at least in part, on the physiological information; notify the patient of the detection of the patient event; and receive a patient response to the notification, the patient response comprising performing at least a first response activity identifiable by the input component and a second response activity identifiable by the input component. The first response activity can comprise an activity configured to test a first patient ability and the second response activity can comprise an activity configured to test a second patient ability, the first patient ability being different from the second patient ability.

Clause 30. The device of clause 29, wherein one of the first patient ability and the second patient ability comprises: cognitive ability, psychomotor ability; movement ability; speech clarity; visual or spatial recognition ability; and reading comprehension.

Clause 31. The device of clause 29 or clause 30, wherein one of the first patient ability and the second patient ability comprises a psychomotor ability.

Clause 32. The device of clause 31, wherein the response activity configured to test psychomotor ability is based on one or more of the following: (a) performing a predetermined gesture or physical action activity; (b) performing a predetermined touch screen activity; and (c) providing a predetermined pressure input.

Clause 33. The device of clause 32, wherein performing a predetermined touch screen activity comprises one or more of: (a) drawing an alpha-numeric character on the touch screen; (b) repositioning, dragging, or moving an image object on the touch screen display to another location on the display; (c) tracing a shape or path on the touch screen; and (d) rotating or manipulating multiple icons or shapes on the touch screen display in a coordinated manner.

Clause 34. The device of any of clauses 29-33, wherein one of the first patient ability and the second patient ability comprises a cognitive ability of the patient.

Clause 35. The device of clause 34, wherein the response activity configured to test the cognitive ability of the patient is based on one or more of general knowledge, short-term memory recall, problem solving and logical reasoning, and visual acumen.

Clause 36. The device of any of clauses 29-35, wherein at least one of the first patient ability and the second patient ability comprises a movement ability of the patient.

Clause 37. The device of clause 36, wherein the response activity configured to test the movement ability of the patient comprises: standing up; walking; picking up and/or moving the device; tapping and/or touching a portion of the device; tapping a portion of the patient's body; maintaining a portion of the patient's body in stable position for a period of time; clapping hands; and stomping feet.

Clause 38. An external medical device comprising: monitoring circuitry configured to sense physiological information of a patient; and a controller comprising one or more input components. The controller can be configured to: detect one or more patient events based, at least in part, on the physiological information; notify the patient of the detection of the patient event; and receive a patient response to the notification, the patient response comprising performing at least a first response activity identifiable by the input component and performing a second response activity identifiable by the input component. The first response activity can be different from the second response activity.

Clause 39. The device of clause 38, wherein the first activity comprises an activity having a first level of difficulty and the second activity comprises an activity having a second level of difficulty.

Clause 40. The device of clause 38 or clause 39, wherein the notification comprises an instruction to perform the first activity and the second activity simultaneously.

Clause 41. The device of any of clauses 38-40, wherein the notification comprises an instruction to perform the first activity and the second activity in sequence.

Clause 42. The device of any of clauses 38-41, wherein the controller is configured to identify one of a partial response activity and an incorrect response activity.

Clause 43. The device of clause 42, wherein the controller is configured to provide a follow-up instruction when one of the partial response and the incorrect response are identified, the follow-up instruction comprising one or more of: (a) an instruction to perform an activity requiring a different patient ability than the response activity that received one of the partial response and the incorrect response; (b) an instruction to perform a different activity requiring the same patient ability as the response activity that received one of the partial response and the incorrect response; (c) an instruction to perform a different activity having a same level of difficulty as the response activity that received one of the partial response and the incorrect response; and (d) an instruction to perform an activity having a lower level of difficulty than the response activity that received one of the partial response and the incorrect response.

Clause 44. The device of any of clauses 38-43, wherein the controller is configured to select one of the first activity and the second activity based on a characteristic of the patient.

Clause 45. The device of clause 44, wherein the characteristic of the patient comprises one or more of: patient technological sophistication; patient education level; diagnosed patient conditions; level of patient training for device operation; patient hearing ability; patient vision ability; current patient physiological status; and the detected patient event.

Clause 46. The device of any of clauses 38-45, wherein the controller is configured to receive the patient response by: instructing the patient to perform the first activity; confirming that the first activity substantially confirms to an expected patient response; and following the confirmation, instructing the patient to perform the second activity.

Clause 47. The device of any of clauses 38-46, wherein the controller is further configured to provide an alert if the patient response activity is not received within a predetermined period of time.

Clause 48. The device of clause 47, wherein the predetermined period of time is less than about two minutes.

Clause 49. The device of any of clauses 38-48, further comprising one or more treatment elements, and wherein the controller is configured to, based on the received response activity, suspend a therapy that is provided via the one or more treatment elements, to address the patient event.

Clause 50. The device of clause 49, wherein the one or more treatment elements comprise therapy electrodes configured to provide defibrillation therapy to the patient.

Clause 51. An external medical device comprises: monitoring circuitry configured to sense physiological information of a patient; a controller comprising an input component. The controller can be configured to: detect one or more patient events based, at least in part, on the physiological information; request a response from the patient, the request comprising instructing the patient to perform a first version of a response activity identifiable by the input component; determine whether a patient response to the request substantially conforms to an expected patient response; and if the patient response fails to substantially conform to the expected patient response, request a subsequent response, the request for the subsequent response comprising instructing the patient to perform a second version of the response activity.

Clause 52. The device of clause 51, wherein the first version of the response activity comprises an activity having a first level of difficulty and the second version of the response activity comprises an activity having a second level of difficulty.

Clause 53. The device of clause 51 or clause 52, wherein the second version of the response activity comprises a simplified version of the first response activity.

Clause 54. An external medical device capable of delivering therapy to a patient, the device comprises: monitoring circuitry configured to obtain physiological information for a patient; therapy circuitry configured to provide a treatment to the patient; an input component configured to detect a patient response activity performed by the patient; and a controller. The controller can be configured to: identify at least one treatable event based on the physiological information from the monitoring circuitry; provide a notification to the patient of an impending treatment in response to identification of the at least one treatable event; and suspend the therapy circuitry from providing the treatment on detecting the patient response activity within a predetermined period of time, wherein the response activity is configured to test at least one of a psychomotor ability and a cognitive ability of the patient.

Clause 55. The device of clause 54, wherein the controller is configured to provide the treatment to the patient when no patient response is received within the predetermined period of time.

Clause 56. The device of clause 54 or clause 55, wherein the controller is configured to identify one or more of a partial response and an incorrect response from the patient.

Clause 57. The device of clause 56, wherein the controller is configured to delay the treatment for a predetermined period of time when one of the partial response and the incorrect response are identified.

Clause 58. The device of clause 57, wherein delaying treatment further comprises providing another notification of impending treatment.

Clause 59. The device of clause 57 or clause 58, wherein the predetermined period of time following one or more of the partial response and the incorrect response is less than about 30 seconds.

Clause 60. A wearable defibrillator comprises: one or more therapy pads operatively connected to a defibrillation shock generator and configured to deliver a defibrillation therapy to a patient; one or more electrodes configured to detect a cardiac activity of the patient; and a controller operatively connected to the defibrillation shock generator and one or more electrodes and comprising an input component. The controller can be configured to: identify a cardiac event treatable by defibrillation therapy based, at least in part, on cardiac activity detected by the one or more electrodes; notify the patient of an impending delivery of the defibrillation therapy; receive a patient response activity from the input component; and suspend the defibrillation therapy if the patient response activity is received within a predetermined period of time. The response activity can be configured to test at least one of a psychomotor ability and a cognitive ability of the patient.

Clause 61. The wearable defibrillator of clause 60, wherein the controller is further configured to cause the defibrillation shock generator to provide the defibrillation therapy to the patient if the patient response activity is not received within the predetermined period of time.

Clause 62. The wearable defibrillator of clause 60 or clause 61, wherein the controller is configured to select the predetermined period of time for receiving the patient response activity based, at least in part, on the cardiac event identified by the controller.

Clause 63. The wearable defibrillator of any of clauses 60-62, wherein the controller is configured to select the predetermined period of time for receiving the patient response based, at least in part, on patient health information for the patient.

Clause 64. The wearable defibrillator of any of clauses 60-64, wherein the predetermined period of time is less than about two minutes.

Clause 65. A method of delivering therapy to a patient using an external medical device, the method comprises: detecting, by an external medical device, a cardiac event of a patient treatable by defibrillation therapy; notifying the patient of impending defibrillation treatment; receiving a patient response activity; and suspending the defibrillation treatment if the patient response activity is received within a predetermined period of time.

Clause 66. The method of clause 65, further comprising providing the defibrillation therapy to the patient when no patient response activity is received, wherein the patient response activity comprises a patient input in response to at least one of a psychomotor ability test and a cognitive ability test of the patient.

BRIEF DESCRIPTION OF THE DRAWINGS

These and other features and characteristics of the present disclosure, as well as the methods of operation and functions of the related elements of structures and the combination of parts and economics of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

FIG. 6B is a flowchart illustrating another patient response scenario using an external medical device;

FIG. 6C is a flowchart illustrating a process for an exemplary input component for identification of a patient response;

FIG. 7 is an exemplary series of patient interface screens for an external medical device illustrating a patient response involving actuation of a response mechanism and performing a psychomotor test;

DETAILED DESCRIPTION

Figure 1:
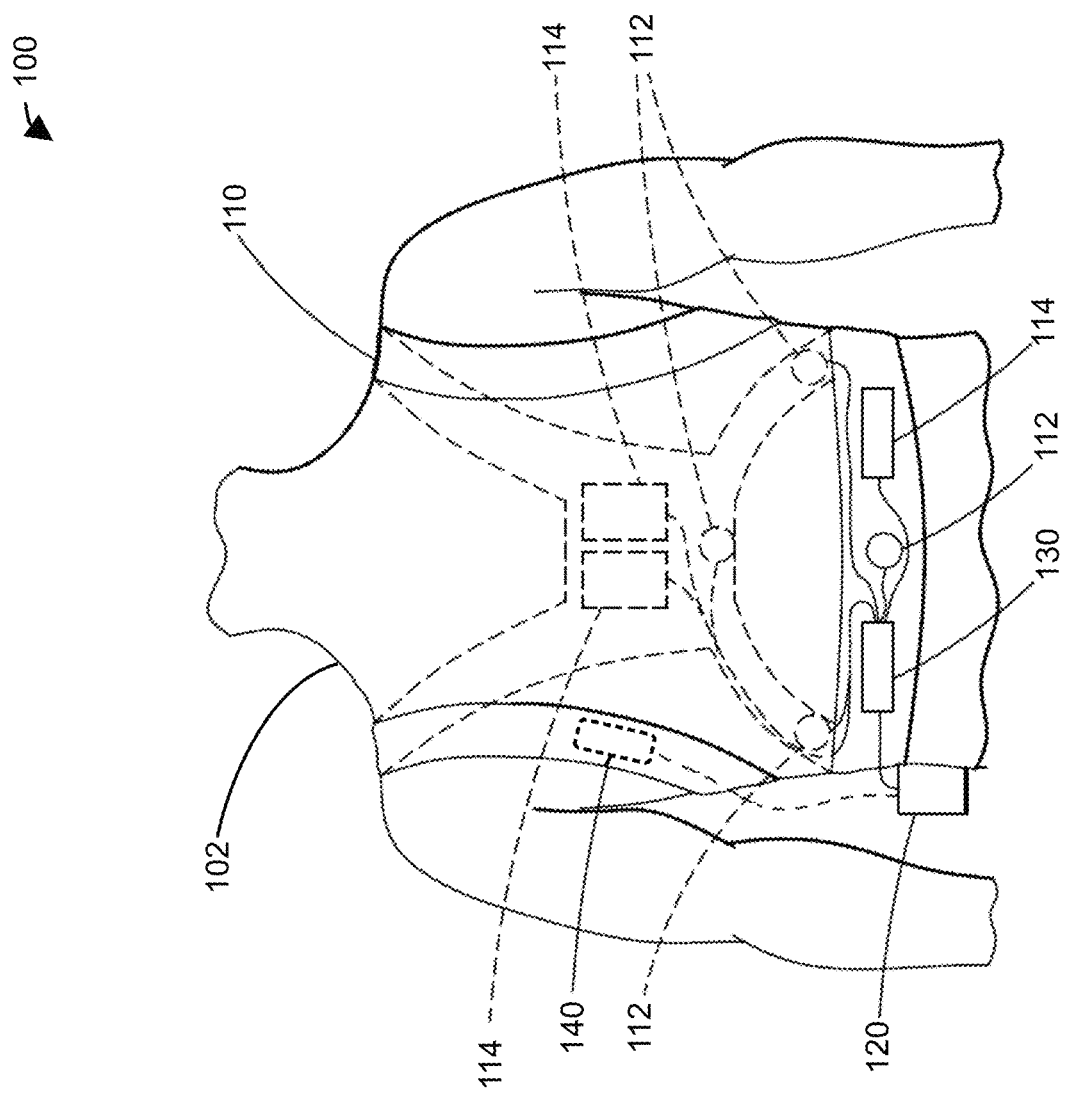
FIG. 1 is an example schematic drawing of a wearable medical device.

As used herein, the singular form of "a", "an", and "the" include plural referents unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Aspects of the present disclosure are directed to monitoring and/or therapeutic medical devices configured to identify a patient physiological event and, in response to the identified event, to provide a notification to the patient wearing the device. The notification can include an instruction or request to perform a patient response activity. Successful completion of the patient response activity can cause the device to suspend or delay a device function, such as administering a treatment to a patient and/or issuing an alert or alarm.

In some examples, the medical device includes monitoring circuitry configured to sense physiological information of a patient. The controller can be configured to detect the patient physiological event based, at least in part, on the sensed physiological information. A patient event can be a temporary physiological problem or abnormality, which can be representative of an underlying patient condition. A patient event can also include injuries and other non-reoccurring problems that are not representative of underlying physiological condition of the patient. A non-exhaustive list of patient events that can be detected by an external medical device includes, for example: bradycardia, ventricular tachycardia (VT) or ventricular fibrillation (VF), atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventricular arrhythmias such as premature ventricular contractions (PVCs) and accelerated idioventricular rhythm.

In some examples, the device controller is configured to notify the patient of the detection of the one or more events and to receive a patient response to the notification. The patient response can include performing a response activity identifiable by an input component associated with the medical device. In general, the response activity is selected to demonstrate or to provide information about the status of the patient and, in particular, to confirm that the patient is conscious and substantially aware of his or her surroundings. The response activity or activities can also be configured to confirm patient identity (e.g., that the person providing the response is the patient, rather than a bystander or imposter). The response activity can also demonstrate or test a patient ability such as one or more of psychomotor ability, cognitive awareness, and athletic/movement ability. In some examples, the response activity can be a relatively simple action, such as making a simple or reflexive movement in response to a stimulus applied by the device. In other examples, more complex activities, such provided answers to questions requiring reasoning and logical analysis can be required. The device can be configured to select a particular response activity based on characteristics of the patient and/or the detected patient event.

In some examples, the device can instruct the patient to perform several actions that are each representative of one patient ability. In other modes, the device can instruct the patient to perform different types of activities that are representative of different patient abilities. For example, the device can instruct the patient to perform a single activity requiring several patient abilities to complete correctly. Alternatively, the device can instruct the patient to perform a first activity representative of a first patient ability and, once the first activity is correctly completed, to perform a second activity representative of a second patient ability.

Example External Medical Devices

This disclosure relates to components, modules, subsystems, circuitry and/or techniques for use in external medical devices. For example, such components, modules, subsystems, circuitry and/or techniques can be used in the context of medical devices for providing treatment to and/or monitoring a patient. For example, such medical devices can include monitoring devices configured to monitor a patient to identify occurrence of certain patient events. In some implementations, such devices are capable of, in addition to monitoring for patient conditions, providing treatment to a patient based on detecting a predetermined patient condition.

In some examples, the medical device can be a patient monitoring device, which can be configured to monitor one or more of a patient's physiological parameters without an accompanying treatment component. For example, a patient monitor may include a cardiac monitor for monitoring a patient's cardiac information. Such cardiac information can include, without limitation, heart rate, ECG data, heart sounds data from an acoustic sensor, and other cardiac data. In addition to cardiac monitoring, the patient monitor may perform monitoring of other relevant patient parameters, including glucose levels, blood oxygen levels, lung fluids, lung sounds, and blood pressure.

Example Therapeutic Wearable Medical Device

With reference to FIG. 1, an example wearable medical device 100, such as a wearable defibrillator, is illustrated. Non-limiting examples of suitable wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944; the disclosure of each of which is incorporated herein by reference in its entirety. The wearable medical device 100 includes a plurality of sensing electrodes 112 that can be disposed at various positions about the patient's body. The sensing electrodes 112 are electrically coupled to a medical device controller 120 through a connection pod 130. In some implementations, some of the components of the wearable medical device 100 are affixed to a garment 110 that can be worn on the patient's torso. For example, the device may be capable of continuous, substantially continuous, long-term and/or extended use or wear by, or attachment or connection to a patient. In this regard, the device may be configured to be used or worn by, or attached or connected to a patient, without substantial interruption, for example, up to hours or beyond (e.g., weeks, months, or even years). For example, in some implementations, such a period of use or wear may be at least 4 hours. For example, such a period of use or wear may be at least 24 hours or one day. For example, such a period of use or wear may be at least 7 days. For example, such a period of use or wear may be at least one month. In some implementations, such devices may be removed for a period of time before use, wear, attachment, or connection to the patient is resumed, e.g., to change batteries, to change or wash the garment, and/or to take a shower. Similarly, the device may be configured for continuous, substantially continuous, long-term and/or extended monitoring of one or more patient physiological conditions. For instance, in addition to cardiac monitoring, the medical device may be capable of monitoring a patient for other physiological conditions. Accordingly, in implementations, the device may be configured to monitor blood oxygen, temperature, glucose levels, sleep apnea, snoring, and/or other sleep conditions, heart sounds, lung sounds, tissue fluids, etc. using a variety of sensors including radio frequency (RF) sensors, ultrasonic sensors, electrodes, etc. In some instances, the device may carry out its monitoring in periodic or aperiodic time intervals or times. For example, the monitoring during intervals or times can be triggered by a patient action or another event. For example, one or more durations between periodic or aperiodic intervals or times can be patient and/or other non-patient user-configurable.

For example, as shown in FIG. 1, the controller 120 can be mounted on a belt worn by the patient. The sensing electrodes 112 and connection pod 130 can be assembled or integrated into the garment 110 as shown. The sensing electrodes 112 are configured to monitor the cardiac function of the patient (e.g., by monitoring one or more cardiac signals of the patient). While FIG. 1 shows four sensing electrodes 112, additional sensing electrodes may be provided, and the plurality of sensing electrodes 112 may be disposed at various locations about the patient's body.

The wearable medical device 100 can also optionally include a plurality of therapy electrodes 114 that are electrically coupled to the medical device controller 120 through the connection pod 130. The therapy electrodes 114 are configured to deliver one or more therapeutic defibrillating shocks, pacing pulses, and/or TENS pulses to the body of the patient if it is determined that such treatment is warranted.

The connection pod 130 may include electronic circuitry and one or more sensors (e.g., a motion sensor, an accelerometer, etc.) that are configured to monitor patient activity. In some implementations, the wearable medical device 100 may be a monitoring only device that omits the therapy delivery capabilities and associated components (e.g., the therapy electrodes 114). In some implementations, various treatment components may be packaged into various modules that can be attached or removed from the wearable medical device 100 as needed. As shown in FIG. 1, the wearable medical device 100 may include a patient interface pod 140 that is electrically coupled to, integrated in, and/or integrated with, the patient interface of the medical device controller 120. For example, the patient interface pod 140 may include patient interface elements such as a speaker, a microphone responsive to patient input, a display, an interactive touch screen responsive to patient input, and/or physical buttons for input.

Figure 2A:
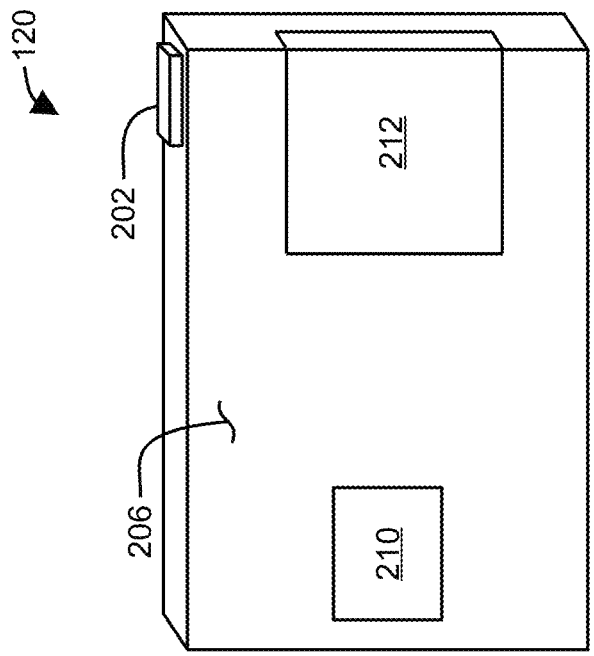
FIG. 2A is a schematic drawing showing a front perspective view of an example monitor for a wearable medical device.
Figure 2B:
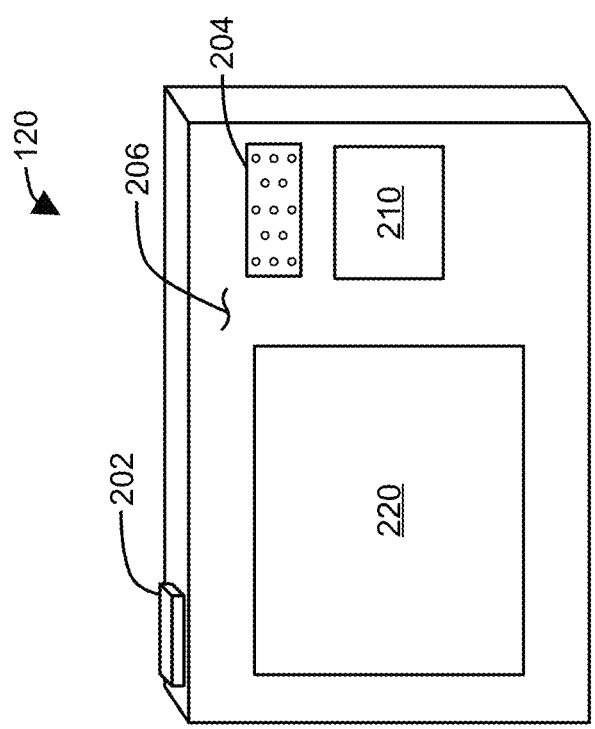
FIG. 2B is a schematic drawing showing a rear perspective view of the example monitor of FIG. 2A.

With reference to FIGS. 2A and 2B, an example of the medical device controller 120 is illustrated. The controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. The controller 120 includes a patient interface such as a touch screen 220 that can provide information to the patient, caregiver, and/or bystanders. In some implementations, in addition to or instead of touch screen 220, the controller 120 may interact with the patient (e.g., receive patient input or provide information to the patient as described herein) via patient interface pod 140 (shown in FIG. 1). The patient interface pod 140 may be operatively coupled to the controller 120. In an example, the controller 120 may be configured to detect that if the patient interface pod 140 is operatively coupled to the controller 120, the controller 120 may then disable the patient interface elements of the controller 120 (e.g., touch screen 220) and instead communicate via the patient interface pod 140. The patient interface pod 140 may be wirelessly coupled with the controller 120. The patient interface pod 140 may take other forms and include additional functionality. For instance, the patient interface pod 140 may be implemented on a smartphone, tablet, or other mobile device carried by the patient. In another example, the patient interface pod 140 may be worn as a watch about the wrist of the patient, or as a band about an upper arm of the patient. In some implementations, the controller 120 may communicate certain alerts and information and/or be responsive to patient input via both the patient interface elements included in the controller 120 and the patient interface pod 140. The patient and/or caregiver can interact with the touch screen 220 or the patient interface pod 140 to control the medical device 100. The controller 120 also includes a speaker 204 for communicating information to the patient, caregiver, and/or the bystander. The controller 120 (and/or the patient interface pod 140) may include one or more response buttons 210. In some examples, when the controller 120 determines that the patient is experiencing cardiac arrhythmia, the speaker 204 can issue an audible alarm to alert the patient and bystanders to the patient's medical condition. In some examples, the controller 120 can instruct the patient to press one or both of the response buttons 210 to indicate that he or she is conscious, thereby instructing the medical device controller 120 to withhold the delivery of therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient. In some examples, as discussed in further detail herein, the controller 120 can additionally or alternatively instruct the patient to perform a response activity to indicate that he or she is conscious and further provide information to the controller 120 regarding the patient's status. For example, the controller 120 can instruct the patient to touch or manipulate the touch screen 220 or an interactive display on the patient interface pod 140 in a coordinated manner to confirm that he or she is conscious and has requisite awareness and/or psychomotor ability. In this way, the patient response confirms not only that buttons 210 were pressed, but that the patient is sufficiently conscious and aware to perform a response activity as instructed. The medical device controller 120 may further include a port 202 to removably connect sensing devices (e.g., ECG sensing electrodes 112) and/or therapeutic devices (e.g., therapy electrodes 114 shown in FIG. 1) to the medical device controller 120.

Figure 3:
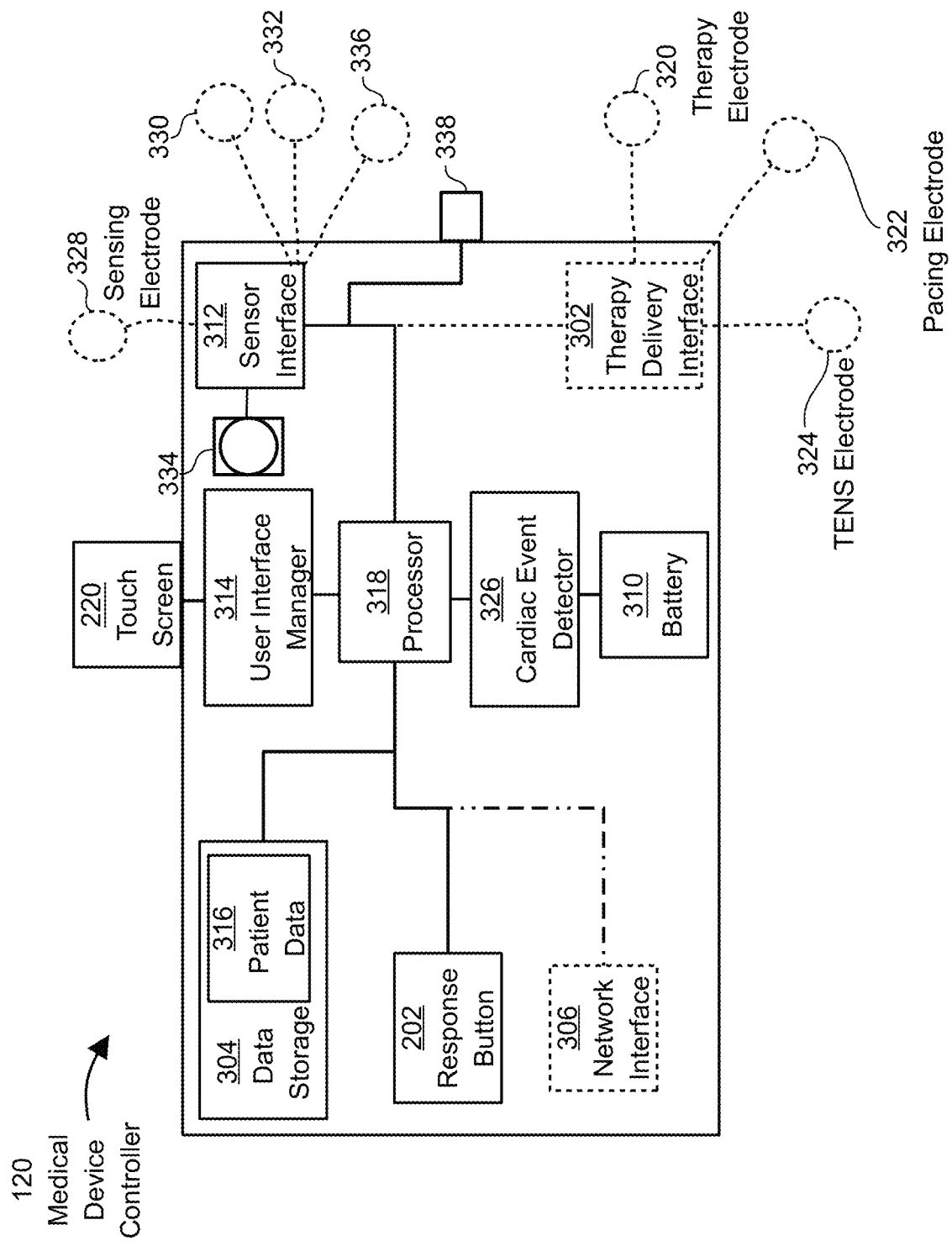
FIG. 3 is a schematic diagram of functional components of a wearable medical device.

With reference to FIG. 3, a schematic example of the medical device controller 120 of FIGS. 1, 2A, and 2B is illustrated. As shown in FIG. 3, the controller 120 includes at least one processor 318, a patient interface manager 314, a sensor interface 312, an optional therapy delivery interface 302, data storage 304 (which may include patient data storage 316), an optional network interface 306, a patient interface 308 (e.g., including the touch screen 220 shown in FIGS. 2A and 2B), and a battery 310. The sensor interface 312 can be coupled to any one or combination of sensors to receive information indicative of cardiac activity. For example, the sensor interface 312 can be coupled to one or more sensing devices including, for example, sensing electrodes 328, contact sensors 330, pressure sensors 332, accelerometers or motion sensors 334, and radio frequency (RF)-energy based sensors 331 (e.g., tissue fluid sensors). The controller 120 can also include an optical sensor 336, such as a digital camera for capturing static or video images of the device surroundings. Although designs from different vendors are different, a digital camera usually consists of a charge-coupled device (CCD) or complementary metal-oxide-semiconductor (CMOS) imaging sensor, a lens, a multifunctional video control chip, and a set of discrete components (e.g., capacitor, resistors, and connectors). The therapy delivery interface 302 (if included) can be coupled to one or more electrodes that provide therapy to the patient including, for example, one or more therapy electrodes 320, pacing electrodes 322, and/or TENS electrodes 324. The sensor interface 312 and the therapy delivery interface 302 may implement a variety of coupling and communication techniques for facilitating the exchange of data between the sensors and/or therapy delivery devices and the controller 120.

In some examples, the medical device controller 120 includes a cardiac event detector 326 to monitor the cardiac activity of the patient and identify cardiac events experienced by the patient based on received cardiac signals. In other examples, cardiac event detection can be performed using algorithms for analyzing patient ECG signals obtained from the sensing electrodes 328. Additionally, the cardiac event detector 326 can access patient templates (e.g., which may be stored in the data storage 304 as patient data 316) that can assist the cardiac event detector 326 in identifying cardiac events experienced by the particular patient (e.g., by performing template matching algorithms).

The at least one processor 318 can perform a series of instructions that control the operation of the other components of the controller 120. In some examples, the patient interface manager 314 is implemented as a software component that is stored in the data storage 304 and executed by the at least one processor 318 to control, for example, the patient interface component 308. The patient interface manager 314 can control various output components and/or devices of the medical device controller 120 (e.g., patient interface 220 and/or patient interface pod 140 shown in FIG. 1) to communicate with external entities consist with various acts and/or display screens described herein. For example, such output components and/or devices can include speakers, tactile and/or vibration output elements, visual indicators, monitors, displays, LCD screens, LEDs, Braille output elements, and the like. Additionally, the patient interface manager 314 can be integrated with the treatment providing components of the controller 120 so that the patient can control and, in some cases, suspend, delay, or cancel treatment using the patient interface.

Example base station for an external medical device

Figure 4:
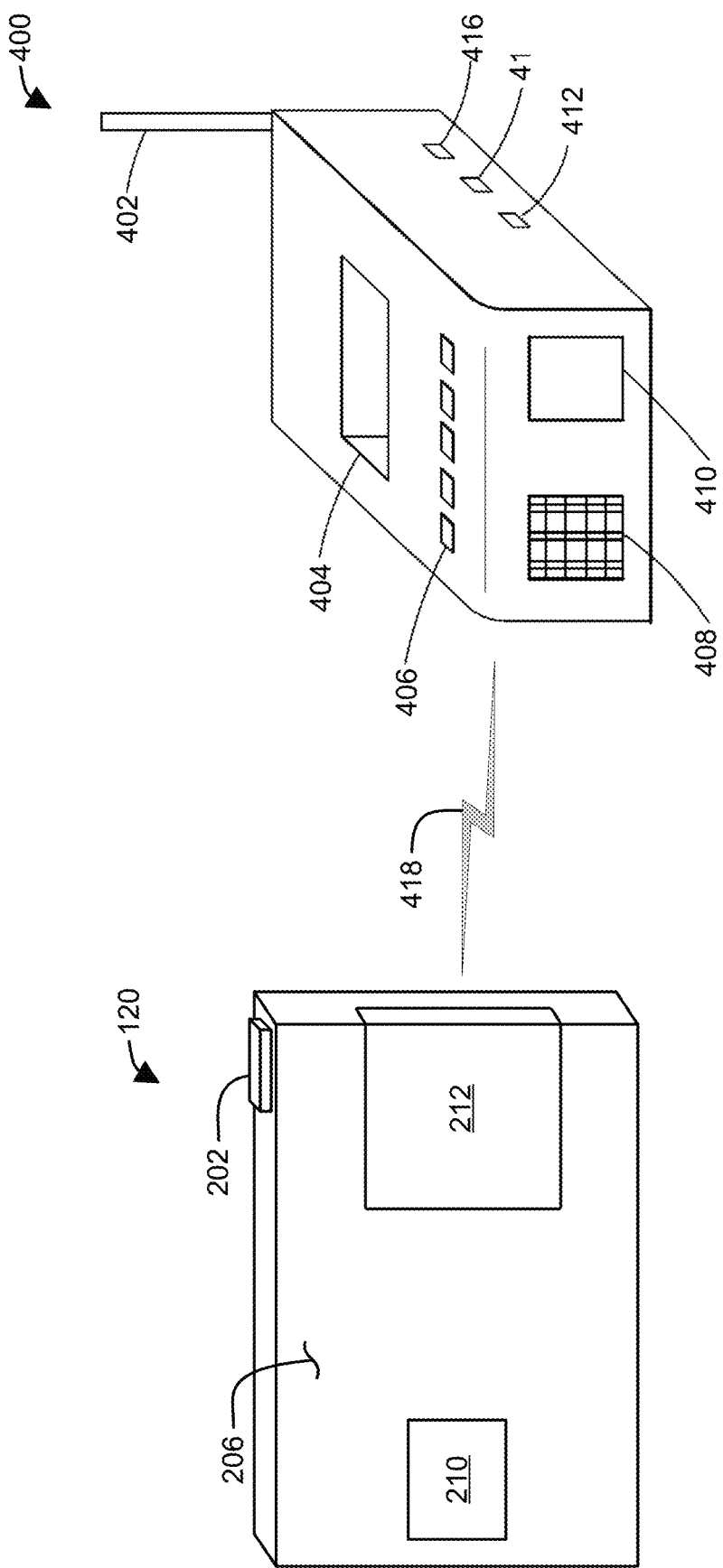
FIG. 4 is a schematic drawing of a patient monitor in communication with a base station.

In some examples, the medical device controller 120 may be in communication with a base station capable of performing a number of different functions. With reference to FIG. 4, an example medical device controller 120 in communication with a base station 400 is illustrated. As illustrated, the base station 400 includes an antenna 402, a battery charging bay 404, one or more buttons 406, a speaker 408, a display 410, and one or more communication interfaces 412, 414, and 416. The base station 400 communicates with the medical device controller via, for example, wired or wireless communication link 418.

In some examples, the base station 400 is capable of charging a rechargeable battery for the medical device controller 120. In these examples, the base station 400 may include a battery charging bay 404 constructed to receive and charge a battery for the medical device controller (e.g., battery 212). The medical device may be provided with multiple batteries to enable a patient and/or caregiver to charge one battery while another charged battery is used to provide power to the medical device. The batteries may be swapped between the medical device controller 120 and the base station 400 once the battery in the medical device controller is depleted (or near depleted). It is appreciated that the base station 400 may include any number of battery charging bays 404 to, for example, charge multiple batteries for the medical device controller 120 simultaneously.

Exemplary Treatment Protocol

Figure 5A:
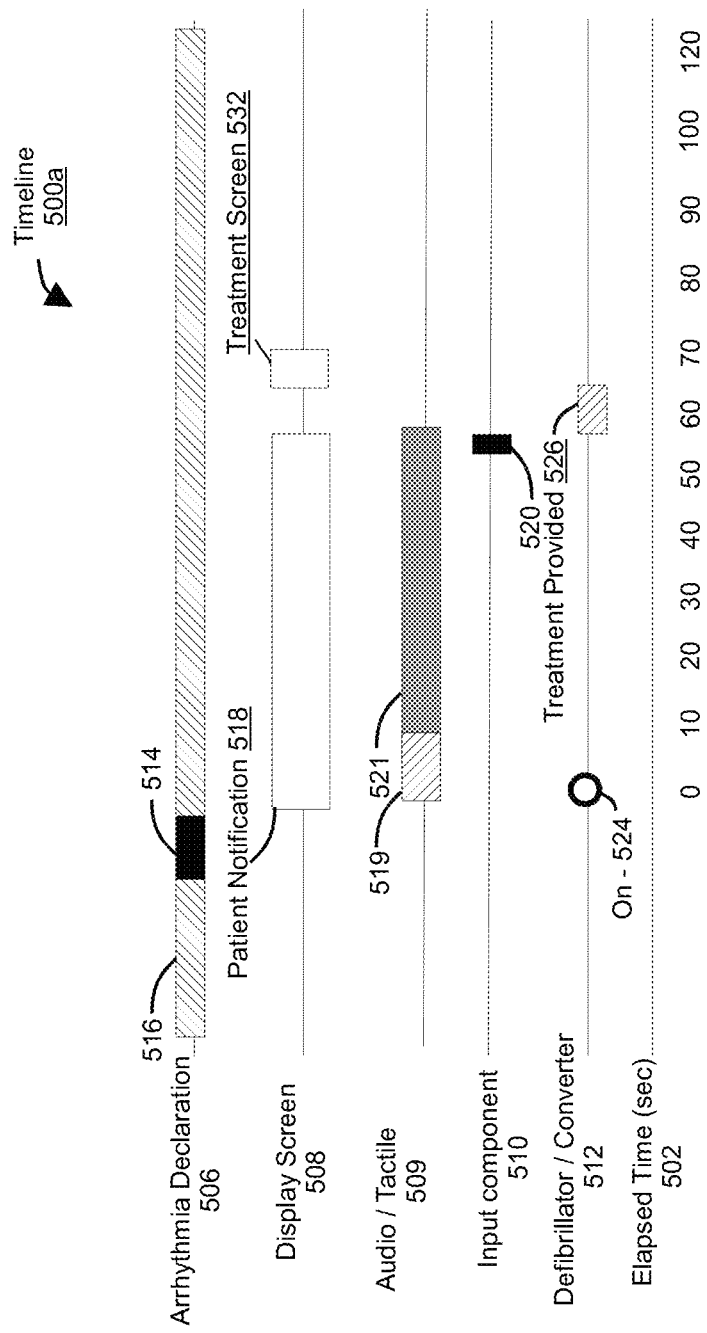
FIG. 5A is a timeline of an example treatment sequence for an external medical device.

Having described the external medical device 100, such as a wearable therapeutic device, and controller 120, timelines 500a, 500b, and 500c illustrating monitoring and providing treatment to the patient over an elapsed time 502 following initial detection of arrhythmia will now be described. With reference to FIG. 5A, the timeline 500a illustrates providing treatment to a patient when the patient fails to provide a response to a patient notification 518. As shown in FIG. 5A, the external medical device 100 (shown in FIGS. 1 to 3) is configured to continuously or substantially continuously receive a signal representative of cardiac activity of a patient. For example, a cardiac signal can be sensed by the sensing electrode 328 (shown in FIG. 3). The received signal can include information representative of occurrence of one or more cardiac events 514, such as a cardiac arrhythmia. The external medical device is configured to detect the arrhythmia event 514 based on analysis of the received cardiac signal, as shown by the analysis activity 516 on the arrhythmia declaration segment 506. In some examples, arrhythmias can be detected using algorithms for analyzing patient ECG signals obtained from the sensing electrodes 328 (shown in FIG. 3). Alternatively or in addition, cardiac events 514 can be detected by template matching techniques based on patient data stored on computer readable memory associated with the device.

Once an event 514 is detected, the device is configured to provide a patient notification 518 on an output component of the device, as shown on the display screen segment 508 of the timeline 500a. For example, the patient notification 518 can include a combination of text and images shown on the touch screen 220 of the device controller 120 or the patient interface pod 140 (shown in FIGS. 1 to 3). As shown on the audio/tactile segment 509, the device controller 120 and/or patient interface pod 140 can also be configured to provide audio and/or tactile notifications and alerts in connection with the patient notification 518. For example, as shown on the audio/tactile segment 509, the device can be configured to vibrate, as shown by box 519, at the same time that the patient notification 518 is shown on the display screen 508 to inform the patient that he or she should review instructions on the screen 220 (or patient interface pod 140) and respond to the patient notification 518. In some examples, if no response to the vibration is received within a predetermined period of time (e.g., about 5 or 10 seconds), as shown at box 521, the device can be configured to emit a recorded sound, such as a siren or gong sound, to provide a more conspicuous indication to the patient that he or she should review and response to the patient notification 518.

In some implementations, the patient notification 518 includes an instruction to actuate a response mechanism, such as response buttons 210 (shown in FIGS. 2A to 3), and/or to perform a response activity with an input component of the controller 120 or patient interface pod 140. In cases in which the response activity involves manipulation of an input component, such as the patient interactive elements of the patient interface pod 140, the touch screen 220, or response button 210 (shown in FIGS. 2A to 3), the input component can be configured to identify and/or confirm the patient's action or selection, as shown by the input component segment 510 of the timeline 500a. Identifying actuation of the response mechanism or performance of the response activity can include, for example, obtaining a signal from the input component and processing the received signal to determine whether it is representative of a patient response to the patient notification 518. If a patient response is received by the input component, the device can confirm that the patient response is in accordance with an expected patient response. For example, if the patient notification 518 asks the patient to provide a password or passcode, confirming the response can include confirming that the code entered by the patient is correct.

As the patient notification 518 is being provided to the patient, the device can be configured to initiate or activate a conversion or defibrillation activity, as shown by the "on" indicator 524 on the defibrillator/converter segment 512 of the timeline 500a. The defibrillator/converter is turned on in preparation for providing therapy to the patient, in the event that a patient response is not received. Turning on and preparing the defibrillator/converter to provide treatment can include, for example, charging the defibrillator capacitors and, if no patient response is received, causing conductive gel to release from the therapy electrodes 320 (shown in FIG. 3), and delivering defibrillation therapy to the patient.

With continued reference to FIG. 5A, if no patient response to the notification 518 is received by the input component as shown at box 520, it can be determined that the patient is unconscious and requires treatment. In that case, the controller 120 can be configured to provide treatment to the patient, as shown at box 526 on the defibrillator/converter segment 512. Following treatment, a treatment provided screen 532, can be shown on the touch screen 220 or patient interface pod 140 (shown in FIGS. 1 to 3) to inform the patient that a treatment has been provided. The treatment provided screen 532 can also include instructions for the patient or a caregiver to follow to ensure that the patient receives appropriate follow-up care following the treatment.

Figure 5B:
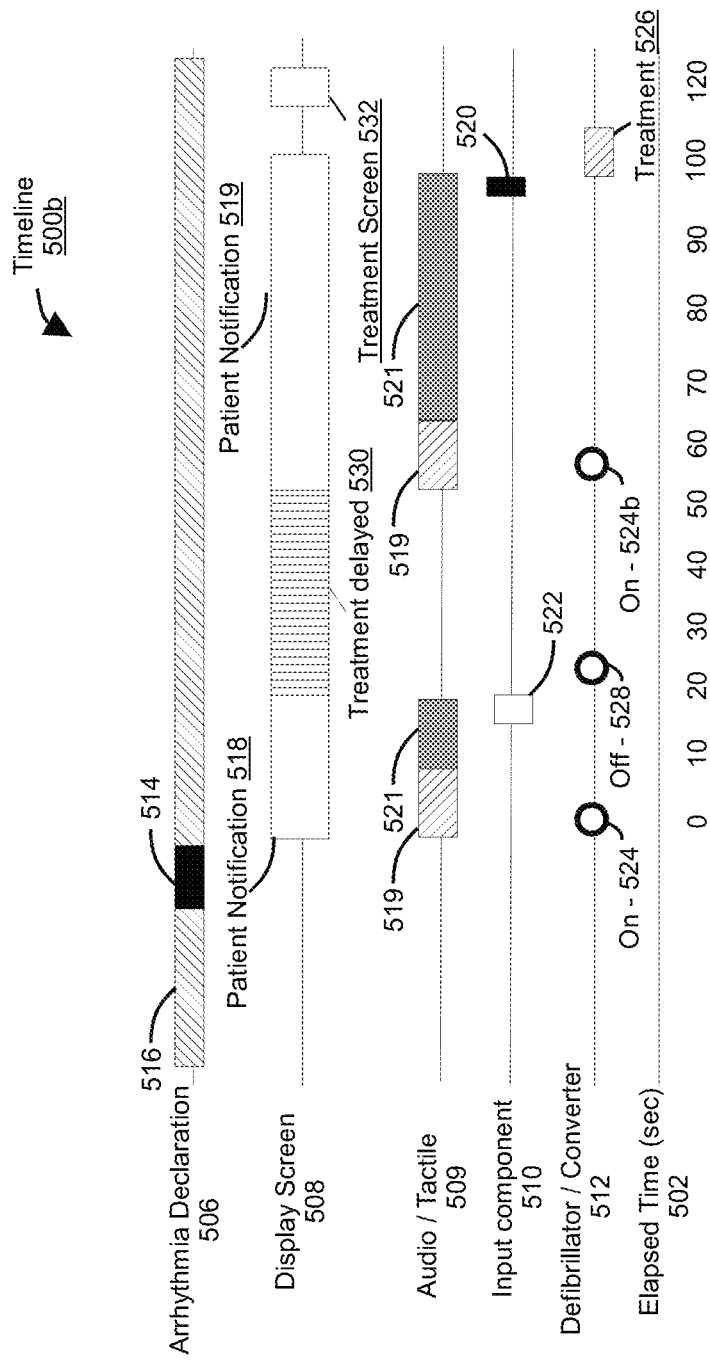
FIG. 5B is a timeline of another example treatment sequence for an external medical device showing treatment being delayed by a patient.

With reference to FIG. 5B, another example timeline 500b is illustrated. As in the previously described example, the cardiac event 514 is identified, as shown by the arrhythmia declaration segment 506. In response to the identified cardiac event 514, the patient notification 518 is provided, as shown on the display screen segment 508. Vibration 519 and audio 521 notifications and/or alerts can also be provided from the controller 120 and/or patient interface pod 140 in connection with the patient notification 518. As discussed above, the patient notification 518 instructs the patient to actuate a response mechanism (e.g., press the response buttons 210) or perform a response activity. If a suitable patient response is received by one of the input components, as indicated by box 522, the device controller 120 can be configured to delay or suspend the treatment sequence. Delaying or suspending treatment can include turning off the defibrillator/convertor, as shown at 528. Turning off the defibrillator/convertor can include, for example, dissipating charge from the treatment capacitors, as well as other activities for returning the device controller 120 to its monitoring and/or non-treatment state. In some implementations, the charge from the treatment capacitors may not be dissipated, rather the charge may be held for a predetermined amount of time in the event such charge is later required for a subsequent treatment. In some examples, a treatment delayed or treatment suspended notification screen 530 can be displayed on the display screen 508 (e.g., the touch screen 220 shown in FIGS. 2A to 3) to inform the patient or bystanders that treatment is delayed or suspended.

In some examples, treatment can be delayed for a predetermined period of time, such as 15 second or 30 seconds. After the predetermined delay time elapses, the controller 120 can be configured to output a second patient notification 519 to confirm that the patient is conscious and does not require therapy. Audio or tactile notifications 519, 521 can be provided in connection with the second patient notification 519, as shown on the audio/tactile segment 509. In addition, as shown on the defibrillator/converter segment 512, the defibrillator/converter can be turned on, as shown at 524b, to prepare to provide therapy to the patient in the event that a patient response is not received.

The second patient notification 519 can request the patient to perform a response activity. The requested activity can be the same or different from the activity requested by the first patient notification 518. For example, the response activity requested by the second patient notification 519 can be a different from a previously requested response activity. In other examples, the response activity requested by the second patient notification 519 can require a different patient ability and/or function than the activity required by the first patient notification 518.

If a suitable patient response to the second patient notification 519 cannot be identified within a predetermined period of time, as indicated by box 520 on the input component segment 510, it can be determined that the patient is unconscious and requires treatment. In that case, the controller 120 can be configured to administer treatment to the patient, as shown at box 526, in the manner described above in connection with FIG. 5A. After the treatment is provided, the controller 120 and/or patient interface pod 140 can be configured to display the treatment provided screen 532 including instructions for the patient and/or bystanders. As shown by the elapsed time 502, the monitoring and treatment routine can last about 2 minutes (120 seconds) from initial identification of the arrhythmia event 514 to providing treatment 526. The number of patient notifications 518 or other confirmation or response activities performed by the controller can vary. In some implementations, the device may be configured to provide treatment, if necessary, within about two minutes.

Figure 5C:
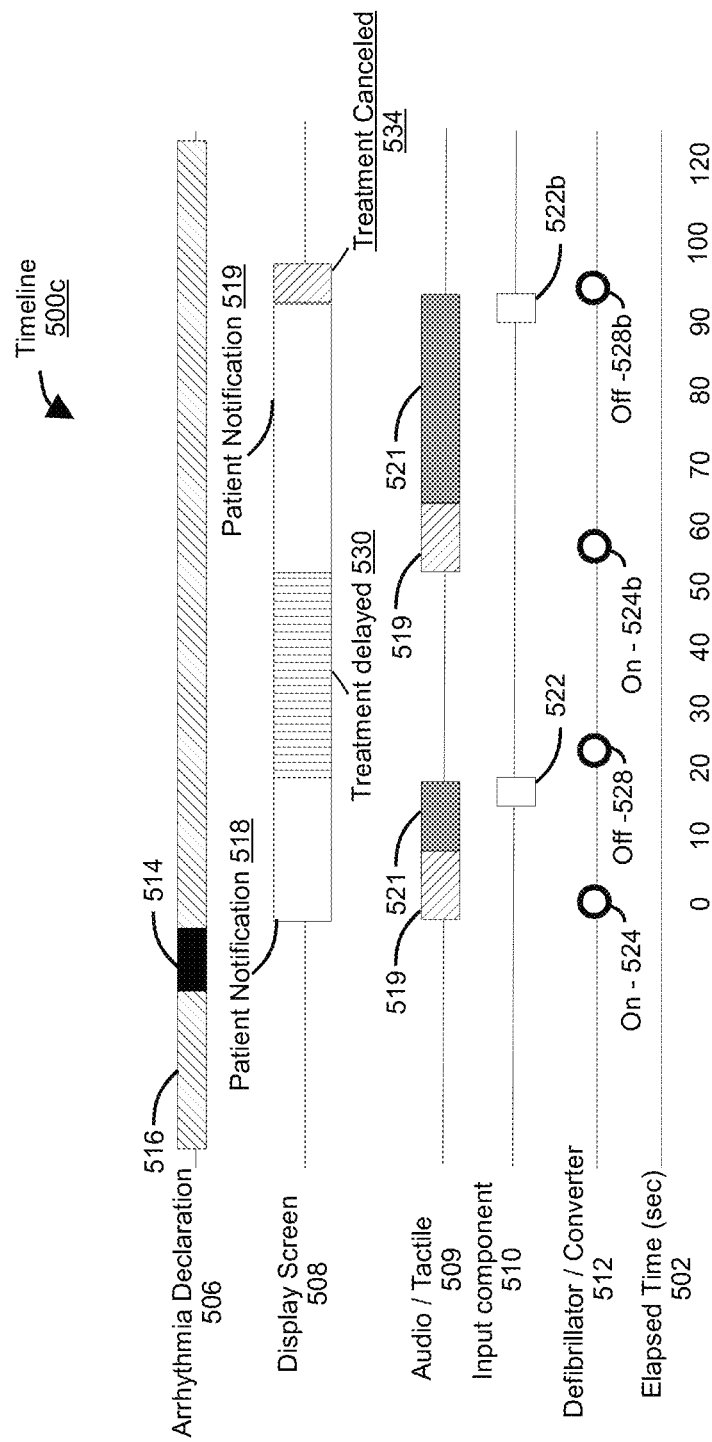
FIG. 5C is a timeline of an example treatment sequence for an external medical device showing treatment being suspended by a patient.

With reference to FIG. 5C, another exemplary timeline 500c is illustrated. In the timeline 500c, the cardiac event 514 is identified by the arrhythmia declaration segment 506 in the manner discussed above. A first patient notification 518 is generated and displayed to the patient and/or non-patient user. In some examples, audio and/or tactile notifications 519, 521 can also be activated, as shown on the audio/tactile segment 509. If a suitable (e.g., expected) patient response is received, as indicated by box 522 of the input component segment 510, treatment can be delayed as described above, in connection with the timeline 500b of FIG. 5B. Following the short delay (e.g., about 10 to 30 seconds) the second patient notification 519 is displayed.

If a suitable patient response to the second notification 519 is received, as indicated by box 522b, the controller 120 can be configured to suspend or cancel treatment. Suspending treatment can include turning off the defibrillator/converter as shown at 528b. As discussed above, turning off the defibrillator/converter can include, for example, dissipating charge from the treatment capacitors, as well as other activities for returning the device controller 120 to its monitoring and/or non-treatment state. In addition to turning off the defibrillator/converter, a treatment suspended screen 534 can be displayed on the display screen 508 to inform the patient or bystanders that treatment has been suspended. The treatment suspended screen 534 can include, for example, text and images informing the patient that the treatment has been suspended and that the device will continue to monitor the patient's condition (e.g., return to a normal monitoring state). In addition, if multiple instances of suspended treatments have occurred, the treatment suspended screen 534 can include troubleshooting instructions for reducing the occurrence of false-positive alerts (e.g., a suggestion to check an electrode connection or wash the garment). In some examples, the treatment suspended screen 534 can include an instruction to contact a patient service representative (PSR) for assistance.

In some examples, a partial or incomplete patient response can be received in response to one of the patient notifications 518, 519. As discussed hereinafter, the device can be configured to delay treatment for a short period of time for each received partial or incomplete response. In some implementations, the device can be configured to periodically or aperiodically ask the patient to perform a response activity to confirm the patient's identity (e.g., enter a passcode or phrase) following a predetermined number of incomplete or partial responses to confirm, for example, that the patient, rather than a bystander, is attempting to use the device. In some examples, the response activities requested by the patient notifications 518, 519 can be made simpler following each incorrect or partial response. In other examples, the type of response activity and/or types of skills required to complete the response activity can be changed following each incorrect or partial response to increase the possibility that a response activity that the patient can complete correctly will be provided.

Exemplary Response Activities

Having generally described the external medical device 100, controller 120, and treatment sequences that can be performed by the external medical device, with reference again to FIG. 3, exemplary patient response activities that can be identified by the device 100 and/or controller 120 will now be discussed. In some examples, a patient response activity comprises one or more actions identifiable by an input component of the device (e.g., the touch screen 220, patient interface pod 140, one or more motion sensors located at various locations on the patient's body, optical sensors, etc.), which are selected to demonstrate and/or to provide information about the status of the patient and, in particular, to confirm that the patient is conscious and substantially aware of his or her surroundings. As will be discussed herein, the type of response activity requested by a patient notification can be dependent upon a variety of factors including the ability of the patient, status of the device, type of condition being monitored for, and/or urgency of providing therapy to the patient.

In some implementations, the response activity comprises performing a single relatively simple action, such as pressing a virtual button displayed on the device touch screen. A patient activity can also be an involuntary movement or reflexive action performed in response to a stimulus or instruction from the medical device. In other examples, the response activity can comprise a more complex activity requiring the patient to perform a predetermined action or gesture in a coordinated manner and/or to provide an answer to a question requiring recall of specific facts and/or logical analysis. The various tests and response activities described herein are provided as examples of the types of patient abilities and conditions that can be determined by the device 100 and/or controller 120.

Psychomotor Test

In some examples, the patient response activity comprises instructing the patient to perform a psychomotor test and/or an action completion of which evidences a psychomotor ability of the patient. Generally, psychomotor activities are based on a relationship between the cognitive functions of the patient and the patient's physical movement. For example, a psychomotor test can require the patient to perform activities demonstrating movement coordination, dexterity, grace, manipulation of tools or instruments, and fine motor skills.

Various psychomotor tests will be described in connection with an input component of the device controller 120 that detects and identifies the response activity provided by the patient. For example, the input component can include one or more of the response button 210; the touch screen 220; an audio detection device, such as the microphone 338; the motion sensor 334, such as an accelerometer or gyroscope; the contact sensor 330; the pressure sensor 332; a gesture recognition component, such as the optical sensor 336; and a patient physiological sensor, such as the sensing electrodes 328.

For response activities indefinable by the touch screen 220, the patient notification can include an instruction to touch or manipulate the touch screen 220 in a coordinated manner. To successfully execute the assigned task, the patient is required to read the instructions on the touch screen 220, determine what area of the touch screen 220 to tap or touch, and contact the touch screen 220 to complete the assigned task. In some examples, performance of the assigned task can merely require tapping a predetermined portion of the touch screen 220, such as a virtual button. In other examples, the patient can be instructed to tap the screen multiple times according to a predetermined pattern. Similarly, the patient can be instructed to slide his or her finger across the touch screen and/or to perform coordinated movements involving a combination of taps and slides. In other examples, the patient can be instructed to record a selection, such as an answer to a multiple choice question, by touching a portion of the touch screen 220 corresponding to a selected answer. For example, activities that can be completed using the touch screen can include one or more of the following: (a) drawing a shape on the touch screen; (b) drawing an alpha-numeric character on the touch screen; (c) dragging or moving an image on the touch screen display to another location on the touch screen; (d) tracing a shape or path on the touch screen; and (e) rotating or manipulating multiple icons or shapes on the touch screen display in a coordinated manner.

In some examples, the response activity is identified by the gesture recognition component, such as the optical sensor 336. A gesture can include a movement or series of coordinated movements in accordance with a predetermined pattern or in response to an instruction from the device. Gestures are generally performed using the patient's fingers, hands, or arms, though gestures involving facial expressions and/or facial movements (e.g., sticking out the tongue or blinking eyes) can also be identified by the gesture recognition component. The gesture recognition component is configured to receive an image from the optical sensor 336 and to process the image to identify whether the image shows the patient performing the gesture of interest. Processing circuitry, such as the processor 318, can be configured to receive and process the received image individually or in combination with signals received from other sensors, such as the motion sensor 334 and/or pressure sensor 332, to detect the gesture.

In some examples, the processing routine can include image processing algorithms for identifying, for example, a position of the patient's hand or fingers in the captured image and for analyzing whether the hands or fingers are moving in the coordinated and predetermined manner. In some cases, the notification of impending treatment from the device can include an instruction to perform a specific gesture. In other examples, the patient can be instructed to perform a specific gesture during initial device training. In that case, the gesture can be used both to test psychomotor ability of the patient and to confirm that the patient, rather than a bystander or companion, performed the gesture. Examples of gestures that can be performed by the patient and recognized by the gesture recognition component can include one or more of: (a) performing a predetermined movement in response to an instruction received from the device; (b) maintaining a predetermined body or hand position for a predetermined period of time; (c) touching or tapping a portion of patient's body or the device in accordance with a predetermined pattern (e.g., the patient can be asked to tap or touch a screen or a portion of the screen a certain number of, say three, times); and (d) performing a predetermined facial expression. In some examples, the coordinated movement can also include moving the device in a coordinated manner. Movement of the device can be identified by the motion sensor 334.

In some examples, the response activity can be identified by the audio input component, such as the microphone 338. For example, the patient can be instructed to speak a predetermined phrase, such as "Stop alarm," or "Stop Treatment". The device can be configured to process a signal received from the microphone 338, to delay treatment when the speech is detected, and based on speech recognition, to confirm that the phrase was spoken by the patient. Example speech recognition techniques that may be implemented are described in, for example, United States Patent Application Publication No. 2016/0004831, entitled "MEDICAL DEVICE WITH NATURAL LANGUAGE PROCESSOR" (hereinafter "the '831 publication"), the contents of which are hereby incorporated herein in their entirety. In other examples, the response activity can include performance of a speech impairment test. For example, the impairment test can include instructing the patient to speak and obtaining a voice recording of the patient's speech for analysis. The analysis can include comparing the recorded speech to a previously recorded sample of the patient's speech to determine whether the patient is speaking in a substantially normal manner. By comparing the recorded speech to a previously recorded version of the patient's speech, the controller 120 can also be configured to confirm that the patient, rather than a bystander, is speaking. Further, the controller 120 can be configured to identify changes in patient speech that indicate a physiological problem or occurrence of a physiological event. For example, changes in speech pattern or quality can indicate conditions such as stroke, brain and neurological injuries, and motor speech disorders.

Cognitive Ability

In some implementations, the patient response activity is selected to demonstrate cognitive ability or cognitive awareness of the patient. Cognitive awareness generally includes a level of consciousness of the patient and, in some cases, can, more specifically, include a patient's ability to process information, recall information, rely on existing knowledge, make decisions, exercise judgment, solve problems, comprehend language, and/or to the patient's level of attention or focus. In some examples, cognitive ability or awareness is evidenced through reading, aural, or visual comprehension, as well as computation and arithmetic ability. For example, activities including recalling phrases or facts, solving riddles, and/or performing mental mathematic calculations are each representative of the cognitive ability of the patient. Cognitive ability can be distinguished from psychomotor ability which focusses on the relationship between mental function and physical movement. Cognitive ability, in contrast, is focused primarily on the patient's ability to process and response to information.

In general, a cognitive ability or awareness test asks the patient to provide a response to an instruction or question requiring cognitive analysis by the patient. For example, the patient notification can include text of a question to be answered by the patient. The response activity can include entering a response to the question using an input component, such as the touch screen 220 of the controller 120. For example, the patient can select a response to a multiple choice question by tapping a portion of the touch screen 220 corresponding to the answer to the question. In other examples, the patient can speak an answer to a question. The microphone 338 can record the patient's response and the controller 120 can process the recorded signal to determine whether the spoken response substantially conforms to an expected response. Similarly, the patient can be instructed to move the device controller 120 in a specific pattern or manner corresponding to an answer to a question. Movement of the controller 120 can be identified by the motion sensors 334 of the controller 120.

In some examples, the response activity (e.g., the answer to the question) is based on the patient's general knowledge of facts or information. General knowledge can include information that is known by many individuals. General knowledge is distinguishable from patient specific information (such as a password, passcode, security question, or preselected security image) that is only known by the patient and, in some cases, a few others. For example, general knowledge can include a patient's knowledge about or recall of time/day/date information; current events information; geography information (e.g., "What city are you currently in?"); visual recognition of shapes, colors, or pictures; recognition of sounds; and recognition of a haptic feedback pattern. For example, the controller 120 can display a picture of a red rectangle. The patient could be asked to select the name of the shape and/or the color of the shape from a list of possible alternatives. The patient could respond to the instruction by tapping a virtual button on the touch screen 220 for the words "Red Rectangle".

In other examples, a test of patient cognitive ability can be directed to the patient's comprehension or calculation ability rather than to specific recall of facts or information. For example, a response activity based on problem solving and logical reasoning ability of the patient can include one or more of: providing a response requiring performance of arithmetic (e.g., "What is 2+7?"); providing a response based on reading comprehension (e.g., an instruction to read a sentence, followed by a question about a fact from the sentence); and providing a response to one of a logic game or riddle.

Movement Ability

In some examples, the response activity tests or evaluates a patient's ability to perform an athletic movement. Such tests are intended to identify the patient's strength, balance, muscle control, and/or speed. In general, such activities do not require the level of coordination required by the psychomotor test and instead, focus on movement and athletic activities that require less thought or planning on the part of the patient. Examples of activities that a patient can be asked to perform for a movement test include one or more of standing up; walking; picking up and/or moving the device; tapping a portion of the device; tapping a portion of the patient's body; maintaining a portion of the patient's body in stable position for a predetermined period of time; clapping hands; and stomping feet. In some examples, the activity is identified by the motion sensor 334. In some examples, the movement activity can include coordinated movement of the controller 120 and/or patient interface pod (shown in FIG. 1). For example, the patient can be instructed to move the device controller 120 and/or patient interface pod 140 in an identifiable manner. In an implementation, the patient can be instructed to lift the controller 120 and/or patient interface pod 140 from a harness or belt of the wearable medical device 100 (shown in FIG. 1) and to shake the controller 120 or patient interface pod 140 a predetermined number of times. Movement of the controller 120 or patient interface pod 140 can be identified by the motion sensors 334.

In other examples, performance of an activity can be identified by a physiological sensor, such as the sensing electrodes 328, heart rate monitor, or audio (e.g., heart sounds) detector associated with the patient and/or device 100. For example, one of the physiological sensors could identify if a patient taps a portion of his or her body. Alternatively, the physiological sensors can be configured to identify physiological changes indicative of performance of a physical activity by the patient. In some examples, strength of the patient can be identified by the pressure sensors 330 and/or contact sensors 332 on the device controller 120. For examples, response activities that can be identified by a pressure and/or contact sensor can include one or more of: pressing against a portion of the device for a predetermined duration; pressing against a portion of the device with a force above a predetermined threshold force; pressing against another object for a predetermined duration; and pressing against another object with a force above a predetermined threshold.

Patient Identification

In some examples, the response activity can comprise a patient identification test. In general, a patient identification test is configured to confirm that the patient rather than a bystander, caregiver, or imposter performs the response activity. Patients are instructed that they should not allow others to operate the external medical device 100 and/or controller 120. In particular, it is important to confirm that the patient is conscious and aware before suspending treatment, and to avoid suspending treatment based on a response from a bystander or caregiver who mistakenly follows instructions or notifications from the device and/or controller 120. One way of confirming that the patient provides the response activity is to select a response activity based on information or knowledge that is only known to the patient or a few others (e.g., patient specific knowledge). For example, the patient notification can instruct the patient to enter certain patient identifying information, such as a passcode or keyphrase using the touch screen 220. Similarly, the notification can instruct the patient to provide a response to a security question preselected by the patient (e.g., "What is your maternal grandfather's first name?"). In other examples, the controller 120 can be configured to detect or record information about the patient to confirm patient identify. For example, the patient could be instructed to perform a predetermined gesture. Sensors associated with the controller 120, such as the optical sensor 336 or motion sensor 334, can record the gesture and confirm that the gesture is correct for the particular patient. Similarly, the microphone 338 can record patient speech. The recorded speech can be compared to a prerecorded version of the patient's speech to confirm that the patient, rather than a bystander or caregiver, is speaking. In still other examples, the device controller 120 can include a biometric sensor or biometric processing routine. For example, the patient can press his or her finger against a fingerprint scanner to confirm patient identity. Similarly, the device controller 120 can be configured to capture an image of the patient with the optical sensor 336 and to process the image to confirm patient identity. Examples of wearable medical devices including biometric sensors used to identify and/or confirm patient identify are disclosed in U.S. Pat. No. 8,271,082, which is assigned to the assignee of the present application and which is incorporated by reference in its entirety.

Adaptable Modes or Tests

Having described the types of response activities that can be provided to confirm patient identify and/or to confirm that the patient is conscious and aware, processes and routines for selecting what type(s) of patient response activities and/or a difficulty level for the response activity will now be discussed in detail. In some examples, the type of response activity is selected by the patient and or by the PSR. In a similar manner, the patient and/or PSR can select a level of difficulty or complexity of the response activity based on a characteristic of the patient. In some implementations, these selections or device settings are entered manually by the PSR during initial device set up and training, and cannot be changed either automatically or by the patient when the device is in the field (e.g., at times when the PSR is not present). In other examples, the device controller 120 can be configured to automatically select a particular type of test or level of difficulty by monitoring the patient's use of the device 100 (e.g., to assess patient aptitude or ability) or based on some measured physiological characteristic of the patient. A number of exemplary routines for assessing patient ability and for updating device settings based on patient ability or status are provided below.

In some examples, a level of difficulty of a patient response activity can be indicated by a length of time needed to complete the assigned task. For example, a task such as pressing a virtual button on a display screen can be performed quickly (e.g., in a few seconds). A task such as connecting dots or drawing a shape on the touch screen of the controller takes a longer time and, as such, has a higher level of difficulty. More involved tasks such as responding to questions, solving a riddle or puzzle, or performing a sequence of movements or gestures require even more time and, as such, have a higher level of difficulty.

In other examples, a level of difficulty may be indicated by an amount of skill or cognitive ability required to perform the task. For example, a relatively simple task, such as pressing a virtual button on a display screen, does not require general knowledge or memory recall and, as such, has a relatively low level of difficulty. Tasks such as providing answers to questions or entering a passcode require the patient to recall information and, as such, have a higher level of difficulty.

The level of difficulty may be assigned by a service technician, PSR, or caregiver. For example, the service technician, PSR, or caregiver may assign a numeric value to different tasks which the device may ask the patient to perform (e.g., 1=easy, 2=intermediate, 3=difficult). In some cases, a level of difficulty for a particular task can be selected based on characteristics of a particular patient. For example, less technologically experienced patients may have difficulty manipulating the device touch screen, but may complete physical activities (e.g., clapping hands, jumping up and down) more easily. For such patients, the tasks requiring use of the fingers or hands to manipulate the device may be assigned a higher level of difficulty than other physical tasks. In contrast, patients with physical disabilities and/or difficulty walking or moving may easily answer questions aurally or by manipulating the device touch screen, but may have difficulty performing more physically involved tasks such as standing up, clapping hands, etc. For such patients, the more physically demanding tasks may be assigned a higher level of difficulty. Exemplary tasks that a patient may perform, along with an anticipated completion time and an assigned level of difficulty for each task, are shown in Table 1.

TABLE 1

| Patient response activity | Anticipated completion time | Level of difficulty |
|---|---|---|
| Touch virtual button on screen | 1 second | 1 |
| Clap hands | 5 seconds | 1 |
| Enter Passcode | 10 seconds | 2 |
| Draw shape on touch screen | 10 seconds | 2 |
| Orally answer security question | 15 seconds | 3 |
| Solve riddle using touch screen | 15 seconds | 3 |

Selecting Response Activities During Device Set Up

As previously described, in some examples, the type of patient response activity and level of difficulty are entered manually by the PSR based on information from the patient and/or on assessment of the patient by the PSR. Based on the information and assessments, the PSR selects settings for the patient response activity and level of difficulty using, for example, a device set up feature of the patient interface. For example, the PSR could consider the patient's medical history (e.g., does the patient have arthritis or diabetes?), aptitude, technological sophistication, education level, and patient's level of experience operating the device when selecting a type of response activity or level of difficulty for a particular patient. For a patient with good memory recall of current events and other information, the PSR can configure the device to ask more difficult questions to evaluate cognitive awareness of the patient. However, for patients that do not have good recall of facts or information, the PSR can configure the device to ask easier questions. In other examples, for patients with poor memory recall, the PSR can configure the device to select response activities that require movement, psychomotor ability, or reading ability, but which do not require the patient to recall specific facts or information. Similarly, for patients that are identified as being particularly technologically experienced or savvy, the PSR may select response activities that require the patient to operate the touch screen 220 to make selections or perform other tasks. For less technologically sophisticated patients, who do not have experience operating touch screen devices, the PSR can select response activities that require less interaction with the touch screen 220. For patients that have a very low level of technological sophistication, the device controller 120 may simply output an audio warning instructing the patient to speak a phrase, such as "Alert Acknowledged" to confirm that he or she has heard and understands the alert.

In some examples, a device or patient assessment test can be provided to assist the PSR in determining characteristics of the patient. In some implementations, the test can be provided on the device controller 120. For example, the assessment test can include a series of questions or instructions to perform various tasks. The patient responds to the questions or tasks using the device and patient responses are identified by the touch screen 220 and/or other device sensors. The assessment could also include asking the patient to practice responding to different types of patient notifications and determining which notifications the patient responds to most easily and/or accurately. In other examples, the PSR can manually administer a test or assessment such as by verbally asking questions to the patient and documenting each correct or incorrect response. Based on the results of the test, the PSR can select device settings and, in particular, types and difficulty levels of the response activities that are best suited for the patient.

For example, the PSR administered test can comprise a series of questions assessing the patient's knowledge of day/date/time information, current events, and/or recall of names of, for example, shapes and colors. If the patient answers such questions substantially correctly, then he or she may be well suited for cognitive awareness tests and/or for tests that require recall of patient identifying information. If the patient is unable to recall such information, then movement tests or low-difficulty psychomotor tests may be more appropriate for the patient. The device and/or PSR could also administer other types of tests such as hearing tests, vision tests, or tests of the patient's ability to operate the device patient interface (e.g., to assess technological sophistication) to determine which types of input and output devices are best suited for a particular patient. Exemplary tests that can be provided to a patient either by an external medical device or by a PSR are discussed, for example, in U.S. patent application Ser. No. 15/374,238, entitled "DEVICE ADMINISTERED TESTS AND ADAPTIVE INTERACTIONS", filed on Dec. 9, 2016, which is incorporated by reference herein in its entirety.

In some examples, baseline characteristics for a particular patient can also be determined, for example, during a patient's meeting with the PSR. For example, baseline values related to a patient's cognitive ability and movement ability can be determined. The baseline value could comprise a score (e.g., on a scale of 1 to 10) indicative of a patient's cognitive ability or movement ability compared to the population generally. Similarly, a recording of the patient's voice could be obtained during this initial meeting. The results of the baseline test and other recorded information can be compared to patient responses given in response to patient notifications when the device is in use. Changes in a patient's cognitive ability could indicate that the patient has experienced a physiological event, such as a stroke. Similarly, changes in speech patterns or movement ability, as evidenced by comparing an initial recording or patient baseline score to a score obtained in response to a patient notification, could be used to confirm that the patient is in distress or, in some cases, to determine a level of physiological distress of the patient.

Learning or Adapting to Patient Use Characteristics

In some examples, the device controller 120 can be configured to automatically tailor the patient response activities for particular abilities or preferences of the patient based on evidence obtained during the patient's use of the device 100. For example, the device 100 can be configured to monitor patient responses to alerts or patient notifications and to assess which types of responses are most often performed quickly and substantially correctly. For example, for patients that have trouble with physical dexterity, responses that can be provided verbally may be preferred and/or most likely to elicit a substantially correct response. However, for patients that are often in noisy environments, responses that can be performed by discretely touching the device (e.g., manipulating the device and/or device touch screen) may be preferred. Further, the device can be configured to monitor how the patient uses the device and, in particular, how the patient uses the touch screens and/or toggles through various patient interface screens. Based on the monitored use, the device controller 120 can automatically update or adjust device settings (e.g. what types of patient notifications are provided and which types and/or difficulty levels of patient response activities are requested) based on evidence of device operation.

In some examples, the device controller 120 can be configured to inform the patient of a selected or recommend type of response activity. For example, if the device controller 120 determines that the patient has trouble operating the touch screen 220, a notification may be displayed recommending that a type of response activity, such as performing a movement or hand gesture, be selected instead. The patient or non-patient user can agree with the change by, for example, selecting a "yes" button on the screen. In other examples, the device controller 120 can be configured to automatically update operating settings without requesting confirmation from the patient.

In some examples, the device controller 120 can be configured to adapt the selected response activity based on the sensed condition of the patient. For example, physiological information about the patient can be assessed based on signals received from the sensing electrodes 328 as well as other sensors 330, 332, 334, 336, 338. The received signals can be used to assess physiological condition of the patient. The device controller 120 can be configured to modify the type and/or difficulty of the patient response activity based on the received physiological information. For example, the device controller 120 can be configured to modify a duration of the delay between providing the notification of impending treatment and the treatment if, for example, the physiological data received indicates that the patient is in substantial physiological distress. Further, in some examples, the received physiological information can be processed to assess or estimate a probability that the patient is in need of a defibrillator shock (e.g., that a shockable rhythm is present). If the physiological information indicates a low or medium probability that a shock is required, a more time consuming test (such as a complex psychomotor test) could be provided to the patient. However, if the processed physiological information indicates a high probability that the patient is in need of treatment, a simpler and faster response activity, such as pressing a virtual button on the touch screen, could be requested. If the patient does not provide the requested response (e.g. tapping the virtual button) within a short period of time, treatment could be provided to the patient without further delay.

Example Patient Monitoring and Treatment Scenarios

Figure 6A:
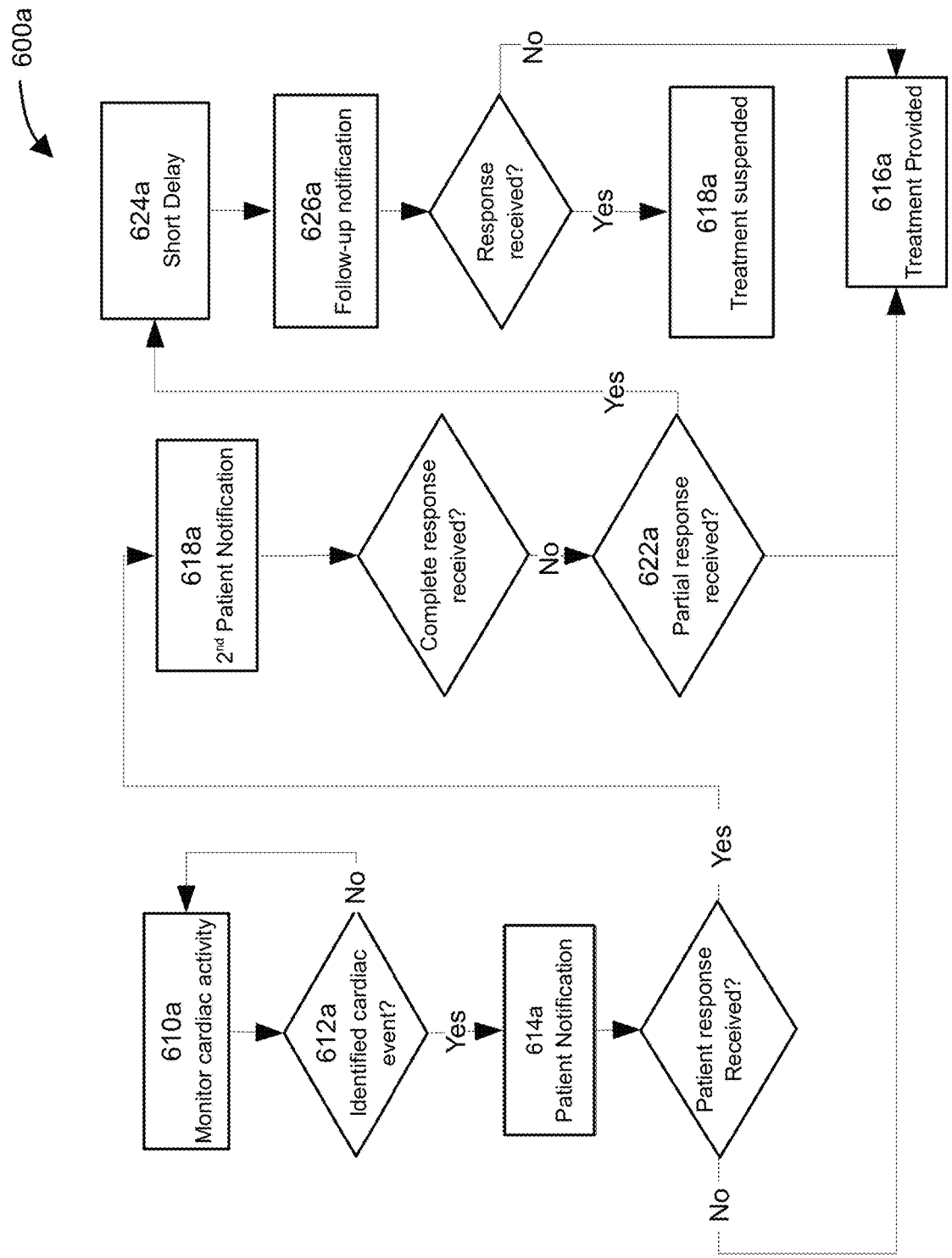
FIG. 6A is a flowchart illustrating a patient response scenario using an external medical device.

Having described the external medical device 100, shown in FIG. 1, and described different types of response activities that can be performed with the device 100, a number of exemplary response sequences for the controller 120 will now be discussed. With reference to FIGS. 6A and 6B, the response sequences 600a, 600b generally include the steps of monitoring cardiac activity 610a, 610b of the patient, identifying a patient physiological event 612a, 612b, providing a patient notification 614a. 614b of impending treatment, and, if no response to the notification is received, providing treatment 616a, 616b to the patient. The response can be identified by an input component of the controller 120. For example, the input component can include or be in communication with one or more of a response button, a touch screen, an audio detection device, a motion sensor, a contact sensor, a pressure sensor, a gesture recognition component, and/or a patient physiological sensor. The input component can be configured to receive and process signals to identify a signal representative of a patient response. An exemplary process that can be performed by the input component for identifying the response is illustrated in FIG. 6C. It is appreciated, however, that the response mechanisms employed by the external medical device controller 120 (shown in FIGS. 2A to 3) may not be limited to the number and type of response activities discussed herein in connection with FIGS. 6A and 6B. For example, scenarios involving more than two response activities or which require the patient to repeat a particular response activity multiple times can be performed within the scope of the present invention. Scenarios in which the patient is required to actuate a response mechanism followed by performance of a response activity can also be envisioned. Further, the device 100 can be configured to implement scenarios requiring only a single response activity or requiring several response activities representative of the same patient ability.

With specific reference to FIG. 6A, the cardiac activity of the patient is monitored as shown at box 610a. Upon detection of the physiological event at box 612a, a first patient notification 614a is provided by the device controller. For example, the notification 614a can require the patient to provide identifying information, such as a passcode. In some implementations, the notification 614a can require a patient to perform a response activity as described above. As the notification is being provided to the patient, the device can initiate a conversion or defibrillation sequence, in preparation for providing therapy to the patient in the event that a patient response is not received. If a patient response to the notification is not received and identified by an input component within a predetermined period of time, the defibrillation sequence can include charging the defibrillator electrodes, applying conducive gel to the patient, and transmitting a shock or pulse to the patient, as shown by treatment provided box 616a.

In some implementations, if a sufficient or substantially correct patient response (e.g., substantially correct performance of the required response activity) is received, the device controller can be configured to suspend the treatment sequence, as shown at box 618a. Alternatively or in addition, the device can be configured to provide a second patient notification, as shown, for example at box 620a. The second patient notification 620a can include an instruction for the patient to perform the same patient activity as was instructed by the first patient notification 614a a second time. In other examples, the second patient notification 620a can include an instruction to perform a different patient activity. The different patient activity can require the same patient ability as the first activity. For example, both activities may test the patient's cognitive abilities and, in some examples, the second patient activity can be a more complex version of the first activity. For example, in the first activity the patient may be required to recall a predetermined passphrase, and in the second activity the patient may be required to perform a quick mathematical calculation. In other examples, the second patient activity can require or be representative of a second type of patient ability. For instance, the first activity may test the patient's cognitive ability, and the second activity may test the patient's psychomotor ability. In this way, the device controller could confirm two types of patient ability prior to determining to suspend treatment to the patient. If a suitable response to the second notification 620a is received and identified by the input component, the device can be configured to delay, suspend or cancel treatment, as shown at box 618a. However, if no response is received, then the device can be configured to provide the therapy to the patient as shown at box 616a.

In some examples, the device can be configured to identify a partial patient response or an incorrect patient response to the notification, as shown at box 622a. A partial response can include, for example, a response that is substantially correct but incomplete. For example, in the case of a passcode, a partial response could include correctly entering the first few characters of the passcode, but omitting the final few characters. An incorrect response can include a response that appears to be complete (e.g., the patient enters the correct number of characters), but is incorrect. A partial or incorrect response can indicate that a patient does not have the mental or physical ability to complete the requested response activity, but is conscious and does not require therapy. Alternatively, the incorrect response can indicate either that the patient is unconscious and the response was entered accidentally (e.g., the patient fell on the device) or that the patient is unconscious and another individual attempted to submit the patient response.

Therefore, in order to confirm or verify that the patient is in need of treatment, in some examples, as shown at box 624a, the device can be configured to delay treatment for a short period of time, such as 15 seconds or 30 seconds. After the short delay 624a, the device can be configured to provide a follow up notification to the patient, as shown at box 626a. The follow-up notification can include a request to perform a different type of response activity. For example, if the patient is unable to complete an activity requiring physical dexterity (e.g., in the case of patient with arthritis) the follow-up activity could require a verbal response from the patient (e.g., instructing the patient to speak "Alert Acknowledged"). If the patient is unable to successfully complete both the activity requiring physical dexterity and the activity requiring a verbal response, it may indicate that the patient is unconscious and that treatment should be provided.

In other examples, the follow-up activity shown at box 626a can include a request to perform an activity that requires the same patient ability with a different level of difficulty. For example, a level of difficulty can be based on an amount of time or number of tasks that must be performed to complete the response activity. Level of difficulty can also be based on an education level, amount of experience using the device, or other characteristics of the patient that impact the patient's ability to correctly complete the response activity. For example, an activity with a low level of difficulty could be to draw a simple shape, such as a circle, on the touch screen. An activity with a higher level of difficulty could be an instruction to draw a circle inside of a square on the touch screen. The second activity requires a higher level of difficulty because (1) two tasks (e.g., drawing the square and the circle) must be completed; and (2) the position of the shapes relative to one another must be considered.

If a patient response to the follow-up notification 626a is received that substantially corresponds to an expected patient response, the treatment can be delayed, suspended or cancelled as shown at box 618a. For example, as discussed above, when a correct response is identified, the device can be configured to reinitiate cardiac monitoring, as shown at box 610a.

If no response to the follow-up notification is received, the device can be configured to continue the therapy sequence by applying conductive gel and causing therapy to be delivered to the patient, as shown at box 616a. If another partial or incorrect patient response is received, the device can be configured to delay treatment for a short period of time and provide a second follow up notification. In some examples, the device controller can be configured to monitor or record a number of partial or incorrect patient responses received by the device within a predetermined period of time. A type of patient notification provided by the device can be selected based on the recorded number of partial or incorrect patient responses. For example, if the patient fails to respond to a movement or psychomotor test on several occasions, the device can conclude that the patient is unable to perform various physical functions. In response, the device can be configured to provide subsequent patient notifications that require only a verbal response. Further, if several incorrect responses in a row are received, it may indicate that the patient is unconscious and accidently contacting a response button or the touch screen. In that case, following the several incorrect responses, the device can cause treatment to be delivered to the patient, as shown at box 616a.

With reference to FIG. 6B, according to another exemplary response sequence 600b, the device monitors cardiac function of the patient, as shown at box 610b. A physiological event is identified at box 612b, in the manner discussed above. In response to the identified event, a patient notification or alert 614b is provided to the patient. However, unlike in the previous example, the notification or alert 614b instructs the patient to actuate a response mechanism, such as the response button 210 (shown in FIGS. 2A to 3). The patient can be instructed to press the response button 210 a single time. Pressing a single button a single time may be particularly appropriate for patients with physical conditions that limit dexterity (e.g., arthritis or diabetes). Alternatively, the patient can be instructed to press and hold the response button 210 for a predetermined duration (e.g., about 10 or 15 seconds). Alternatively, the patient can be instructed to press a response button multiple times in quick succession. In other examples, the patient can be instructed to press multiple response buttons simultaneously.

If the patient does not actuate the response button within a predetermined period of time, the device can be configured to provide treatment by delivering a shock to the patient as shown at box 616b. However, if the patient actuates the response buttons 210 (shown in FIGS. 2A to 3) in the instructed manner, the device can be configured to delay treatment for a short period of time. During the short delay, the device can provide another patient notification, as shown at box 620b. The second notification can instruct the patient to perform a response activity. As described above, the response activity can be configured to test or demonstrate one or more of psychomotor ability of the patient, cognitive ability of the patient, and movement ability of the patient. The patient response to the second notification 620b can be identified by the device controller by the input components in the manner described above.

If a patient response is received that substantially corresponds to an expected patient response, the device controller can be configured to delay, cancel or suspend treatment as shown at box 618b. If a partial or incorrect response is received, the device can be configured to delay treatment for a short period of time and/or to provide a follow-up notification in the manner discussed in connection with FIG. 6A. If no response is received, the device can provide treatment to the patient as shown at box 616b.

With reference to FIG. 6C, a process 650 that can be performed by an exemplary input component for receiving and identifying a patient response is illustrated. As shown at box 652, the input component receives and monitors signals to identify a signal representative of a patient response. For example, signal can be received from one or more of a touch screen, an audio detection device, a motion sensor, a contact sensor, a pressure sensor, a gesture recognition component, and a patient physiological sensor. The screens and/or sensors can be associated with the input component and/or device controller or can be a separate device in communication with the input component. Monitoring is continued until a signal representative of a patient response is identified, as shown at box 654. For example, in the case of a touch screen, identification of the patient response can include processing a signal from the touch screen to identify a signal indicative of contact with a portion of the touch screen. For audio detection devices, identification of a signal representative of a patient response can include processing signals received from the audio detection device to differentiate a signal representative of a patient response from background noise and/or other sounds recorded by the audio detection device. When a patient response is identified, the response can be communicated to the device controller, as shown at box 656, for further processing and analysis. For example, as discussed in connection with FIGS. 6A and 6B, the identified response can be compared with an expected patient response to confirm whether the identified patient response substantially conforms to the expected response.

Example Operational Sequences and Patient Interface

With reference to FIGS. 7-to 10, exemplary patient interfaces that can be displayed to the patient on, for example, the touch screen 220 (shown in FIGS. 2A to 4) or another visual display are illustrated. The patient interfaces can be controlled, for example, by the patient interface manager 314 (shown in FIG. 3). The patient response mechanism can be partially or completely integrated with the patient interface. For example, the patient interfaces can be configured to provide the patient notification to the patient and can receive the patient response activity for the purpose of initiating, delaying, suspending, or cancelling a process performed by the device.

It is appreciated that the screens and screen sequences described below are for illustration only and should not be construed as being the only way to implement the concepts described herein. For example, in the context of screens for providing an instruction or test to the patient, the sequence of screens or the screens themselves can be changed from those shown in FIGS. 7 to 10 to include other types of questions or to include different icons to be manipulated by the patient without departing from the spirit of the concepts described herein.

Patient Response Mechanism Followed by Patient Response Activity

With specific reference to FIG. 7, a sequence of screens for instructing the patient to respond to a first notification by actuating a response mechanism, such as the response buttons 210 (shown in FIGS. 2A to 3), and to a second patient notification by performing a response activity are illustrated. The device is configured to provide a patient notification screen 710 when a patient event, such as identification of a cardiac arrhythmia or shockable rhythm is detected. For example, the screen 710 can include a text notification 714 stating, for example, "Event Detected!" and, in some cases, informing the patient of impending treatment. The screen 710 can also include text instructing the patient to actuate a response mechanism, such as the response button 210. The screen 710 can also include a static image or animation illustrating, for example, the location of the response button 210 on the device and/or how the button should be pressed. In some examples, the patient can be instructed to press multiple response buttons simultaneously. In other examples, the patient can be instructed to press one response button multiple times or in a predetermined pattern.

In some examples, if the response button 210 is pressed within a predetermined period of time (e.g., about 30 seconds), the device 100 is configured to delay, suspend or cancel treatment. If the patient fails to press the response button 210 as instructed, the device can be configured to advance to a providing treatment screen 712. For example, the screen 712 can indicate that treatment is being performed and can also include instructions for bystanders, such as a warning 716 to "Stand Back". Audio alerts instructing bystanders to stand back can also be provided from the device at the same time that the treatment screen 712 is displayed. After a delay of a few seconds to allow bystanders to respond the providing treatment screen 712, the controller 120 (shown in FIGS. 2A to 3) generate a signal to cause the treatment to be provided to the patient.

If the patient correctly presses the response button 210 within the required period of time, the device can be configured to provide a second notification. The second notification can be configured to instruct the patient to perform a response activity. For example, the device can display a patient response screen 720 including an instruction to perform a task representative of, for example, psychomotor ability and/or cognitive ability of the patient. It should be noted that in some implementations, after an event is detected, instead of requesting the patient to press a response button, the patient interface manager and/or controller 120 can be configured to immediately progress to and present screen 720 to the patient.

In some examples, the task or response activity can include drawing or tracing a figure on the touch screen display. As shown in screen 720, a series of dots 722 are illustrated. The patient is instructed to trace a path by connecting the dots 722 as described by explanatory text 724. The patient can complete the task by touching the screen 720 at a first dot and, while maintaining contact with the touch screen display, tracing a path connecting each of the series of dots 722.

If the patient response substantially corresponds to an expected response (e.g., the path connects the dots in the correct order), the controller 120 can be configured to suspend or delay treatment. In that case, a treatment suspended screen 732 can be displayed. The treatment suspended screen 732 can inform the patient that treatment is suspended and that the device is returning to its normal patient monitoring state.

Figure 10:
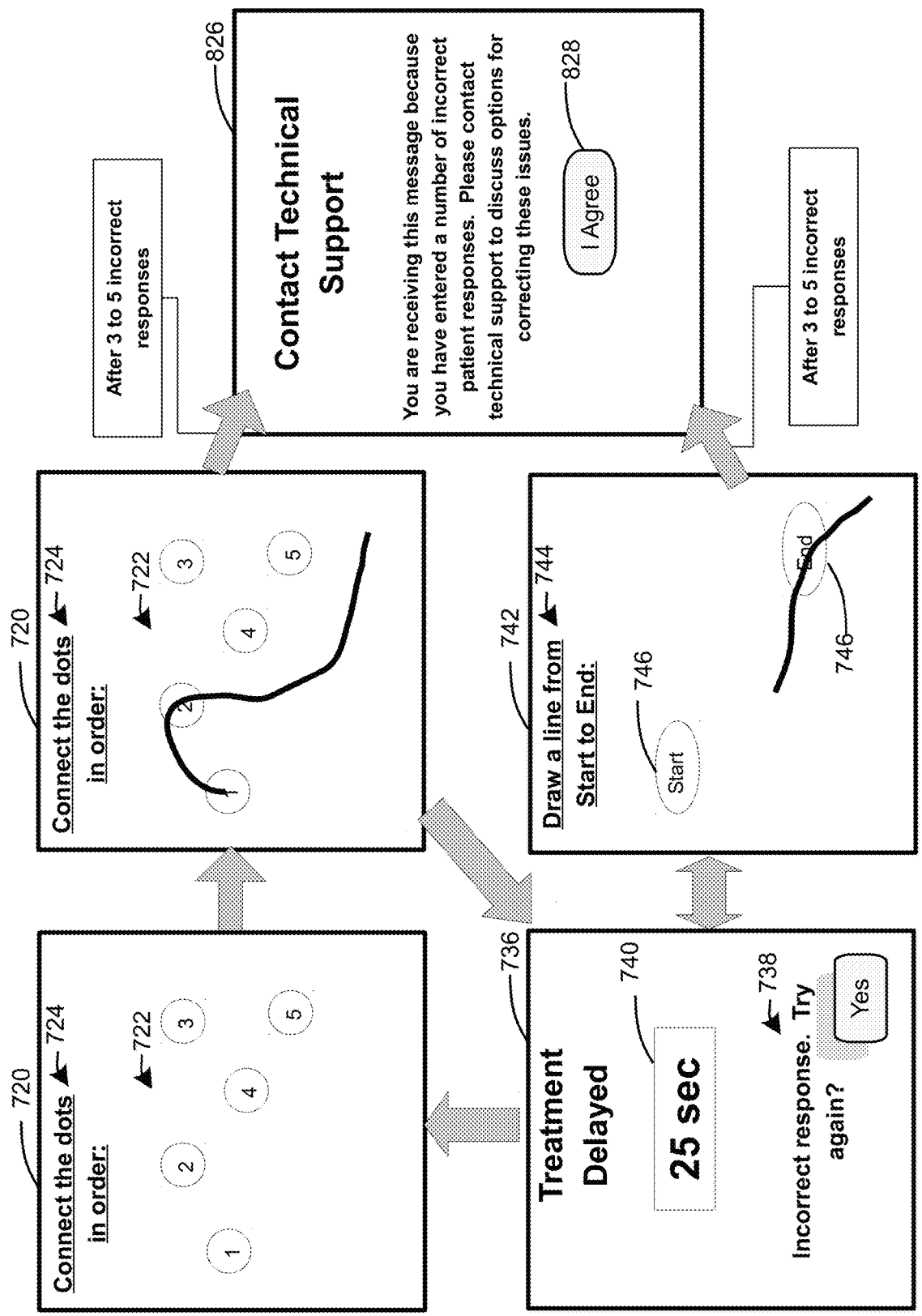
FIG. 10 is an exemplary series of patient interface screen for an external medical device instructing a patient to contact technical support when multiple partial or incorrect responses are received.

If a patient response is received, but does not substantially correspond to the expected response (e.g., the patient touches the screen but fails to connect the dots), the patient may be asked to perform the task again. If, given a second opportunity, the patient successfully completes the task, treatment can be suspended, as shown in screen 732. If no response is received, treatment may be provided to the patient as discussed below. If the patient continues to provide a response (e.g., the patient touches the screen when instructed to do so), but fails to complete the task when given several opportunities (e.g., about 3 to 5 opportunities) then the device may suspend treatment, as the continued registered responses indicate that the patient is conscious but unable to manipulate the device to perform the task. In that case, the patient may be instructed to contact technical support to adjust the device and/or to select another response sequence that he/she can perform correctly when required to do so. A screen 826 instructing the patient to contact technical support is shown in FIG. 10. As shown in FIG. 10, the patient is asked to confirm by pressing the "I Agree" button 828, that he/she will contact technical support as instructed. In other examples, the device may continue to ask the patient to perform the task until either (i) the patient successfully completes the task as instructed or (ii) the cardiac event (e.g., ventricular fibrillation) is no longer detected by the monitoring circuitry. When the cardiac event is no longer detected, the contact technical support screen 826 can be displayed to the patient as described herein.

With continued reference to FIG. 7, if no patient response is received by the touch screen 220, the controller 120 can be configured to advance to the providing treatment screen 712 and/or to produce an audible alarm indicating the treatment is about to be provided. A few seconds after the treatment screen 712 is displayed, the controller 120 can be configured to cause treatment to be provided to the patient.

After treatment is completed, the patient interface can be configured to provide a treatment completed screen 726. The screen 726 can inform the patient and bystanders that treatment is completed. The screen 726 can also include instructions that the patient or a bystander should follow for caring for the patient after the treatment is administered. For example, appropriate care can include seeking medical attention immediately. The patient or a bystander can also be instructed to call the patient's PSR to check the status of the device to confirm that the device is operating normally following the treatment event. The screen 726 can also ask the patient to acknowledge that he or she understands, such as touching an "Agree" button 728. Once the patient acknowledges that the instructions on the treatment completed screen 726 have been reviewed, the patient interface can return to a main menu or home screen and the medical device can continue to monitor the patient in the manner discussed hereinabove.

Identify Partial Patient Activity

Figure 8:
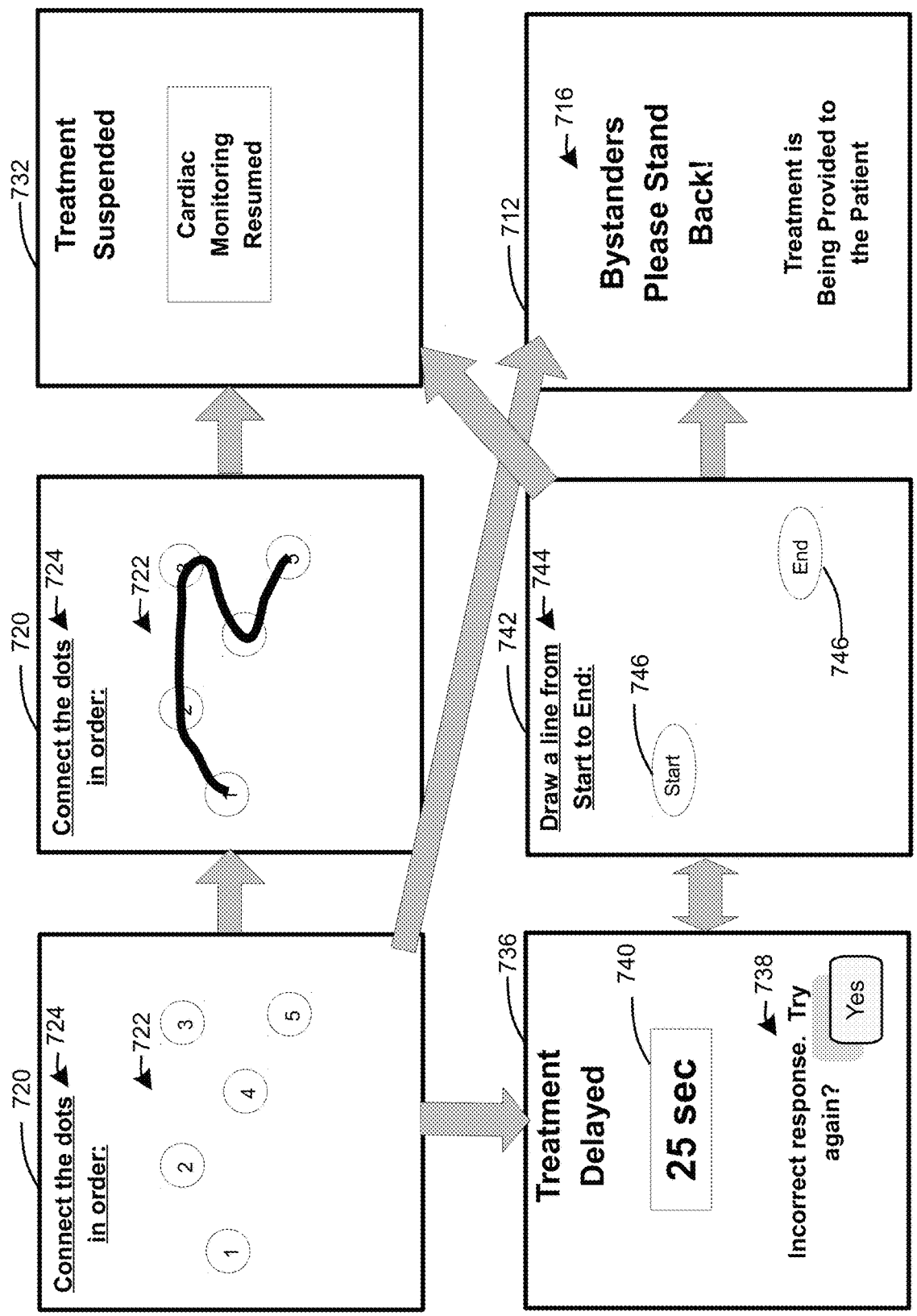
FIG. 8 is an exemplary series of patient interface screens illustrating a follow-up patient notification in response to a partial or incorrect patient response.

In some examples, the controller 120 (shown in FIG. 3) can be configured to evaluate both whether any contact with the touch screen registered and, if contact is registered, whether the contact substantially completes the instructed task. As described hereinabove, responses that do not substantially conform to an expected response can be referred to as partial or incorrect responses. With reference to FIG. 8, a series of patient interface screens for identifying and following up on a partial or incorrect response is illustrated. As shown in FIG. 8, a response screen 720 including a series of dots 722 is illustrated. As in the example described in connection with FIG. 7, the patient is instructed to trace a path by connecting the dots 722 as shown by explanatory text 724. The patient can complete the task by touching the screen at a first dot and, while maintaining contact with the touch screen display, tracing a path 730 connecting each of the series of dots 722. The controller 120 can be configured to evaluate (1) whether the traced path 730 begins and ends in the correct locations and (2) whether the path 730 substantially contacts each of the dots. If the path 730 satisfies each of the criteria, then the treatment suspended screen 732 can be displayed.

If the controller 120 identifies that some contact with the touch screen display occurred, but that the contact did not amount to successful completion of the instructed task (e.g. successfully connecting all of the dots with the path 730), the controller 120 can identify the response as a partial or incorrect response. For a partial or incorrect response, a treatment delayed screen 736 can be displayed to the patient. The treatment delayed screen 736 can inform the patient that the response was incorrect and that treatment has been delayed, as shown by explanatory text 738. The treatment delayed screen 736 can also include a countdown clock or icon 740 counting down until the patient will be given another opportunity to respond to a patient notification.

After the predetermined delay elapses (e.g., the clock or timer 740 reaches 0), a follow-up response screen 742 can be displayed to the patient. In some examples, the follow-up notification screen 742 can include text 744 instructing the patient to perform another response activity. The text 744 can instruct the patient to perform a simplified version of the response activity that the patient did not complete correctly. For example, as shown on the follow-up screen 742, the patient can be instructed to draw a line connecting two dots 746. This follow-up activity may be, in some implementations, less complex then the activity requested in screen 720, in which the patient was instructed to draw a path between a series of dots 722.

If the patient successfully completes the follow-up activity, the controller 120 is configured to suspend treatment and the treatment suspended screen 732 is displayed to the patient. If another partial or incorrect response is received, the controller 120 can display another treatment delayed screen 736 and/or another follow-up patient notification 742. For example, as discussed above, the subsequent follow-up notification can ask the patient to provide a patient response representative of another patient ability. As long as partial or incorrect responses are being provided, the controller 120 may be configured to provide notifications to the patient to perform response activities. Because partial or incorrect responses indicate that the patient is conscious, the device may continue to suspend or delay treatment as long as such responses are received. Periodically or aperiodically, e.g., every second or third activity, the device may provide a patient identification activity or other mechanism that is configured to confirm that the person performing the activity or responding to the notification is the patient and not a bystander.

In some examples, the controller 120 may continue to ask the patient to submit a response until (i) a correct response to the follow-up notification screen 742 is received, (ii) no response is received indicating that the patient is unconscious or incapacitated, or (iii) the identified patient event (e.g., ventricular fibrillation) is no longer present. When the controller 120 determines that the event is no longer present, the user interface may display a screen instructing the patient to contact technical support. An exemplary screen 826 instructing the patient to contact technical support is shown in FIG. 10.

If no response is received to the follow-up display screen 742, the controller 120 can be configured to provide treatment to the patient. After treatment is provided, the treatment provided screen 712 can be displayed in the manner described above.

In some examples, rather than continuing to delay treatment indefinitely when the patient enters an incorrect or partial response, the controller instead may suspend treatment following a number of incorrect or partial responses. For example, as shown in FIG. 10, a contact technical support screen 826 may be displayed if the patient enters a large number of incorrect responses. More specifically, as shown in FIG. 10, when an event is first identified, the notification screen 720, which asks the patient to connect the dots in order, is provided. If the patient enters a response (e.g., by touching the display screen) but fails to complete the assigned task, a treatment delayed screen 736 is displayed. Following the delay (e.g., the 25 second delay in screen 736), the patient is either asked to complete the task again or to complete a simplified version of the task (e.g., drawing a line between two dots). For example, the screen 720 instructing the patient to connect the dots may be displayed after the 25 second delay. Alternatively, a simplified display screen 742 may be displayed asking the patient to perform a simplified version of the task. If the patient does not complete the activity (e.g., either connecting the dots or drawing a straight line between the dots 746) several times in a row (e.g., about 3 to 5 times), the controller may suspend treatment and provide a notification screen 826 instructing the patient to contact technical support. Specifically, as shown in FIG. 10, the screen 826 informs the patient that he/she has submitted an incorrect response on several occasions and asks the patient to confirm, by pressing button 828, that he/she will contact technical support. Technical support may examine the patient's device to assess whether there are any issues which are preventing the patient from providing a correct response to the notification screens 720, 742. Alternatively or in addition, technical support may consider whether there are other patient response activities which may be easier for the patient to perform correctly within the time allotted for response.

Response Activity Including Patient Confirmation

Figure 9:
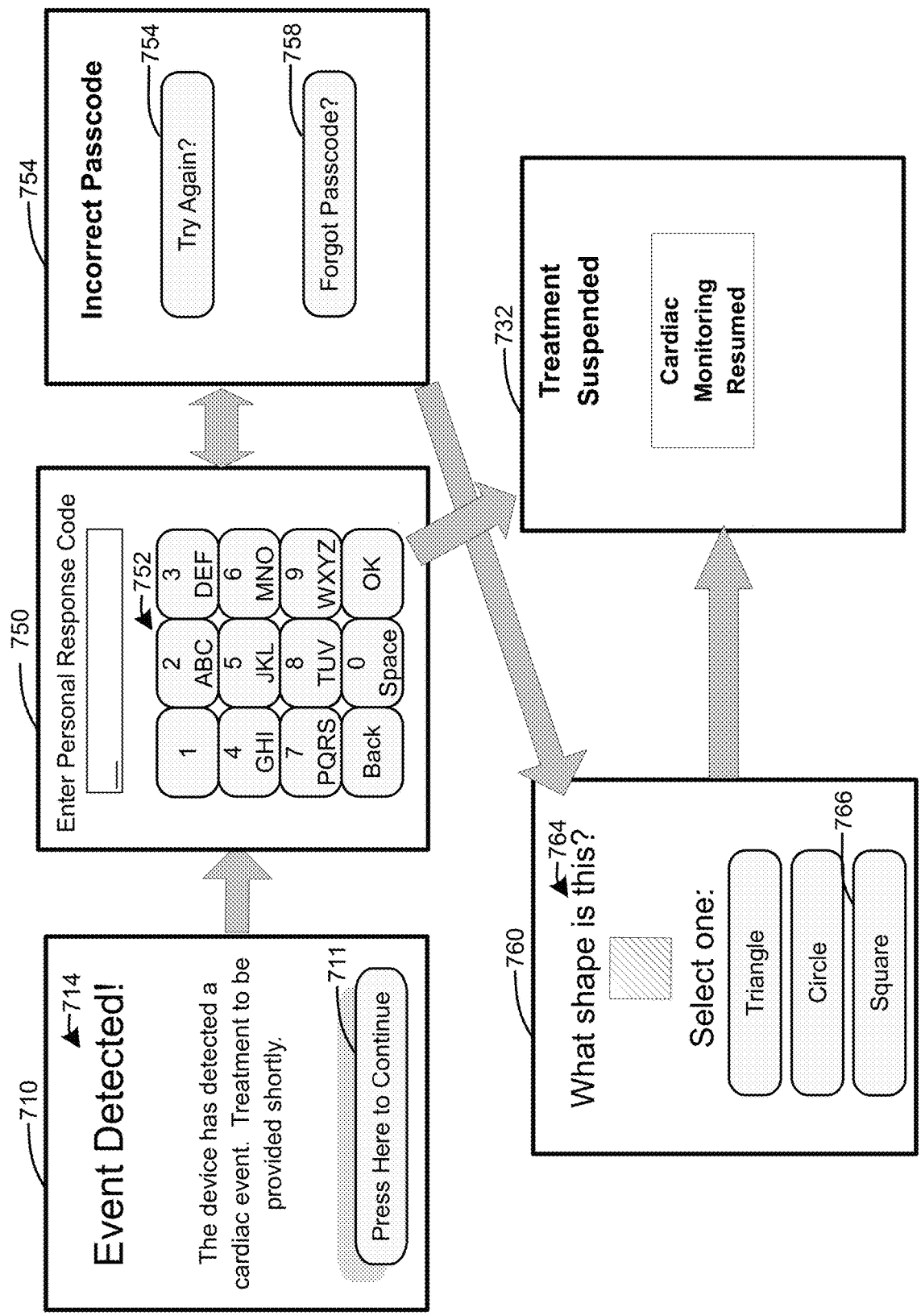
FIG. 9 is an exemplary series of patient interface screens for an external medical device including a patient response activity to confirm patient identity.

With specific reference to FIG. 9, a sequence of patient interface screens for instructing the patient to perform a response activity to confirm patient identify is illustrated. As discussed previously, when a treatable event, such as ventricular fibrillation, is identified, as shown at screen 710, the notification 714 can appear stating "Event Detected!" and, in some cases, informing the patient of impending treatment. The patient interface can be configure to advance to a sequent patient response activity screen either automatically, such as after a predetermined period of time (e.g. about five seconds) or upon registering a button press of the Continue button or arrow 711.

The patient response screen 750 can include an instruction to perform a task or response activity configured to confirm that the person performing the activity is the patient. For example, the patient response screen 750 can include an instruction to enter the patient's personal passcode. The passcode can be a unique four digit number that the patient provides or is given during initial device set up. The passcode can be, for example, the last four digits of the patient's social security number, last four digits of a phone number, or another easily remembered series of numbers. The screen 750 can also include a virtual number pad 752 that allows the patient to enter the passcode using the touch screen 220 (shown in FIGS. 2A to 3) of the controller 120.

As in previously described examples, the controller 120 (shown in FIG. 3) can be configured to evaluate (1) whether any response is received from the patient and (2) whether the response substantially confirms to an expected response (e.g., whether the passcode is correct). If the passcode is entered incorrectly, as shown at screen 754, a virtual button 756 asking the patient if he or she would like to make another attempt to enter the passcode can be displayed. The screen 754 can also include a "Forgot Password?" button 758.

In some examples, if the patient selects the "Forgot Password?" button 758, the controller 120 can be configured to request a different type of information from the patient. For example, a screen can be displayed including a question based on patient specific information, such as asking the patient to enter his or her birthdate, birth city, mother's maiden name, spouse's name, or other identifying information that would not be known by a bystander. Similarly, as shown at screen 760, a cognitive awareness test could be provided to the patient to assess if the patient is conscious and aware of his or her surroundings. The screen 760 can include one or more questions evidencing general knowledge or memory recall of the patient. For example, an image of a shape (e.g., square) and an instruction 764 for the patient to select what shape is depicted from a list of available alternatives. The patient can complete the test by selecting a virtual button 766 corresponding to the correct response to the question or instruction.

If the passcode and/or response to the cognitive awareness test are received and substantially conform to an expected response, the controller 120 can display the treatment suspended screen 732, as described above. The treatment suspended screen 732 alerts the patient that the task or response activity is successfully completed and that no treatment will be administered.

If the patient fails to enter the correct passcode and does not provide a correct answer to the cognitive awareness test, the controller 120 can be configured to provide treatment to the patient in the manner discussed above in connection with FIGS. 7 and 8. After treatment is provided, a treatment completed screen 726 (shown in FIG. 7) can be displayed, instructing the patient and/or bystanders in steps to take following treatment.

The embodiments have been described with reference to various examples. Modifications and alterations will occur to others upon reading and understanding the foregoing examples. Accordingly, the foregoing examples are not to be construed as limiting the disclosure.

What is claimed is:

1. A wearable monitoring and treatment device for testing patient abilities, the device comprising:
    a garment configured to be worn on a torso of a patient;
    therapy electrodes supported by the garment and operatively connected to a shock generator configured to deliver an electrical therapy to the patient;
    one or more sensors supported by the garment configured to detect physiological information of the patient;
    at least one response button;
    a touch screen display; and
    a controller operatively connected to the shock generator, the one or more sensors, the at least one response button, and the touch screen display, wherein the controller is configured to:
        select at least one patient response action configured to test cognitive ability of the patient from a plurality of possible response actions that test cognitive ability and an associated level of difficulty for the at least one patient response action based on information provided by at least one of a service technician, a patient service representative, or a caregiver;
        identify a patient event treatable by shock therapy based, at least in part, on physiological information detected by the one or more sensors;
        upon detection of the patient event, instruct the patient to perform, with the at least one response button or the touch screen display, the selected at least one patient response action configured to test the cognitive ability of the patient; and
        suspend the shock therapy when a complete or partial patient response action is received.

2. The device of claim 1, wherein the electrical therapy delivered to the patient by the therapy electrodes comprises at least one of a therapeutic defibrillation shock, pacing pulses, and/or TENS pulses.

3. The device of claim 1, wherein the therapy electrodes are configured to release conductive gel prior to delivery of the electrical therapy to the patient.

4. The device of claim 1, wherein the one or more sensors comprise ECG sensing electrodes configured to sense patient ECG signals.

5. The device of claim 1, wherein the one or more sensors comprise heart sound sensors configured to sense heart sounds of the patient.

6. The device of claim 1, wherein the one or more sensors comprise radio frequency (RF) sensors configured to sense signals representative of tissue fluid in one or more lungs of the patient.

7. The device of claim 1, wherein the therapy electrodes and/or the one or more sensors are in wired connection with the controller through one or more ports disposed on the controller.

8. The device of claim 1, further comprising a controller housing configured to house the controller, and wherein the controller housing comprises the at least one response button.

9. The device of claim 1, further comprising a user interface pod separate from a controller housing configured to house the controller and in wired or wireless communication with the controller.

10. The device of claim 9, wherein the user interface pod comprises the at least one response button.

11. The device of claim 10, wherein the user interface pod further comprises one or more of a speaker, a microphone responsive to patient input, a visual display, or an interactive touch screen responsive to patient input.

12. The device of claim 1, wherein the patient event identified by the controller comprises one or more of: bradycardia, ventricular tachycardia, ventricular fibrillation, atrial fibrillation, and/or supraventricular tachycardia.

13. The device of claim 1, wherein the physiological information comprises at least one of: patient heart rate, ECG data, heart sounds data, glucose levels, blood oxygen levels, lung fluids, lung sounds, or blood pressure.

14. The device of claim 1, wherein the selected at least one patient response action configured to test the cognitive ability of the patient comprises an action configured to test at least one of: a general knowledge of the patient, a short-term memory recall ability of the patient, a problem solving and logical reasoning ability of the patient, or a visual acumen of the patient.

15. The device of claim 1, wherein the selected at least one patient response action comprises a first patient response action configured to test the cognitive ability of the patient and a second patient response action configured to test psychomotor ability of the patient, and wherein the second patient response action comprises one or more activities configured to test one or more of strength, balance, stability, and flexibility of the patient.

16. The device of claim 1, wherein the selected at least one patient response action comprises a first patient response action configured to test the cognitive ability of the patient and a second patient response action configured to confirm an identity of the patient, and wherein the second patient response action comprises at least one of: providing a predetermined passcode or keyphrase; providing a response to a security question preselected by the patient; or answering a question requiring patient-specific information.

17. The device of claim 1, wherein the controller is configured to suspend the therapy when the complete or partial response is received within a predetermined period of time.

18. The device of claim 17, wherein the controller is further configured to cause the shock generator to deliver the electrical therapy to the patient when no indication is received that the patient performed or attempted to perform the patient response action within the predetermined period of time.

19. The device of claim 1, wherein, when the received response action is the partial patient response action, the controller is further configured to provide a follow-up instruction to the patient comprising one or more of: (a) an instruction to perform an action requiring a different patient ability than the patient response action; (b) an instruction to perform a different action requiring the same patient ability as the patient response action; (c) an instruction to perform a different action having a same level of difficulty as the patient response action; and/or (d) an instruction to perform an action having a lower level of difficulty than the patient response action.

20. The device of claim 1, wherein when the received response action is the partial patient response action, the at least one controller is configured to:
    provide a follow-up instruction to the patient comprising an instruction to perform a second patient response action having a different level of difficulty than the level of difficulty for the selected at least one patient response action; and suspend the shock therapy when a complete or partial patient response to the second patient response action is received.

\* \* \* \* \*